United States Patent
Ohki et al.

Patent Number: 5,569,646
Date of Patent: Oct. 29, 1996

[54] POLYPEPTIDE COMPOUND AND A PROCESS FOR PREPARATION THEREOF

[75] Inventors: Hidenori Ohki, Ikeda; Masaki Tomishima, Minoo; Akira Yamada, Fujiidera; Hisashi Takasugi, Sakai, all of Japan

[73] Assignee: Fujisawa Pharmaceutical Co., Ltd., Osaka, Japan

[21] Appl. No.: 242,854

[22] Filed: May 16, 1994

[30] Foreign Application Priority Data

May 17, 1993 [GB] United Kingdom .................. 9310091
Dec. 10, 1993 [GB] United Kingdom .................. 9325269

[51] Int. Cl.$^6$ .......................... A61K 38/00; C07K 7/00; C07K 7/06
[52] U.S. Cl. ................. 514/11; 514/9; 530/317; 530/329
[58] Field of Search ................. 530/317; 514/9, 514/11

[56] References Cited

U.S. PATENT DOCUMENTS

| | | | |
|---|---|---|---|
| 5,159,059 | 10/1992 | Balkovec et al. | 530/317 |
| 5,166,135 | 11/1992 | Schmatz | 514/11 |
| 5,376,634 | 12/1994 | Iwamoto et al. | 514/9 |
| 5,386,009 | 1/1995 | Hammond et al. | 530/317 |

FOREIGN PATENT DOCUMENTS

| | | |
|---|---|---|
| 0431350 | 6/1991 | European Pat. Off. |
| 0462531 | 12/1991 | European Pat. Off. |

*Primary Examiner*—Elizabeth C. Weimar
*Assistant Examiner*—S. G. Marshall
*Attorney, Agent, or Firm*—Oblon, Spivak, McClelland, Maier & Neustadt, P.C.

[57] ABSTRACT

A polypeptide compound having antifungal activities of the following general formula:

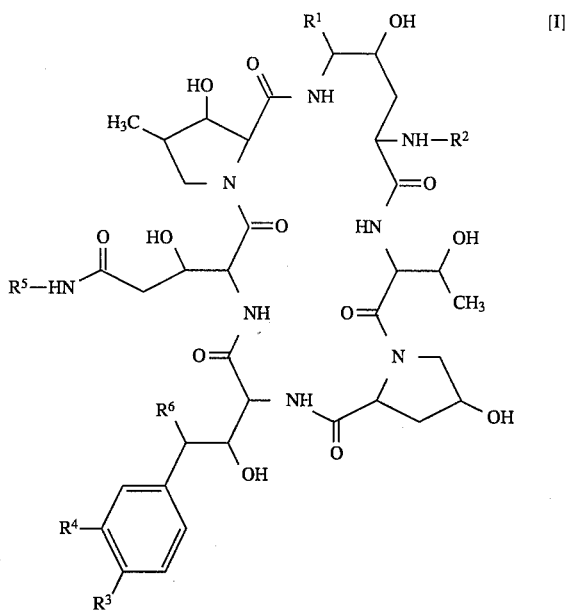

wherein $R^1$ is hydrogen
$R^2$ is acyl group,
$R^3$ is hydroxy or acyloxy,
$R^4$ is hydroxy or hydroxysulfonyloxy,
$R^4$ is hydrogen or lower alkyl which may have one or more suitable substituent(s), and
$R^6$ is hydrogen, hydroxy or acyl (lower) alkylthio and a pharmaceutically acceptable salt thereof.

7 Claims, No Drawings

POLYPEPTIDE COMPOUND AND A PROCESS FOR PREPARATION THEREOF

The present invention relates to new polypeptide compound and a pharmaceutically acceptable salt thereof.

More particularly, it relates to new polypeptide compound and a pharmaceutically acceptable salt thereof, which have antimicrobial activities (especially, antifungal activities), inhibitory activity on β-1,3-glucan synthase, and further which are expected to be useful for the treatment or prevention of *Pneumocystis carinii* infection (e.g. *Pneumocystis carinii* pneumonia) in human being and animals, to a process for preparation thereof, to pharmaceutical composition comprising the same, and to a method for treating or preventing infectious diseases including *Pneumocystis carinii* infection (e.g. *Pneumocystis carinii* pneumonia) in human being and animals.

Accordingly, one object of the present invention is to provide the polypeptide compound and a pharmaceutically acceptable salt thereof, which are highly active against a number of pathogenic microorganisms and further which are expected to be useful for the treatment or prevention of *Pneumocystis carinii* infection (e.g. *Pneumocystis carinii* pneumonia) in human being or animals.

Another object of the present invention is to provide a process for the preparation of the polypeptide compound and a salt thereof.

A further object of the present invention is to provide a pharmaceutical composition comprising, as an active ingredient, said polypeptide compound or a pharmaceutically acceptable salt thereof.

Still further object of the present invention is to provide a method for treating or preventing infectious diseases including *Pneumocystis carinii* infection (e.g. *Pneumocystis carinii* pneumonia) caused by pathogenic microorganisms, which comprises administering said polypeptide compound to human being or animals.

The object polypeptide compound of the present invention is novel and can be represented by the following general formula [I]:

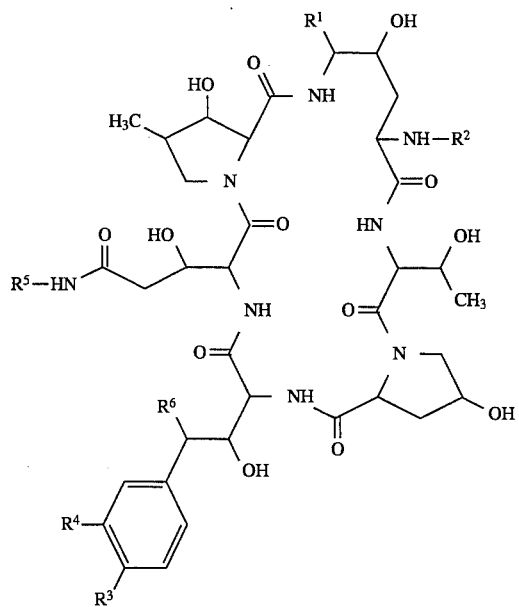

wherein $R^1$ is hydrogen, $R^2$ is acyl group, $R^3$ is hydroxy or acyloxy, $R^4$ is hydroxy or hydroxysulfonyloxy, $R^5$ is hydrogen or lower alkyl which may have one or more suitable substituent(s), and $R^6$ is hydrogen, hydroxy, or acyl (lower) alkylthio.

The polypeptide compound [I] of the present invention can be, prepared by the processes as illustrated in the following scheme.

Process 1

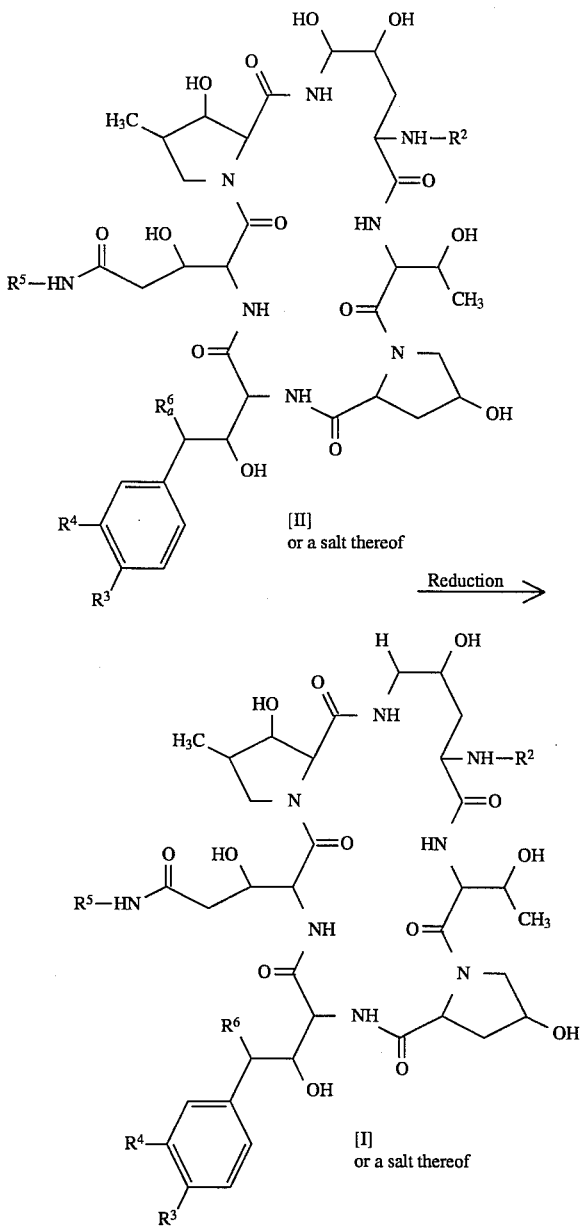

3
Process 2 -continued
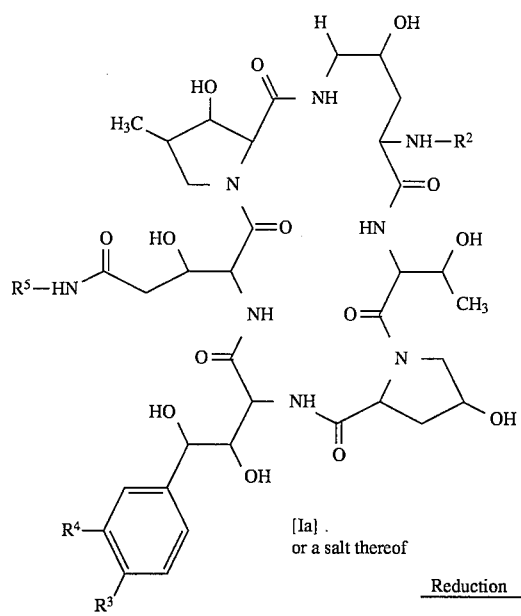
[Ia]
or a salt thereof
Reduction →
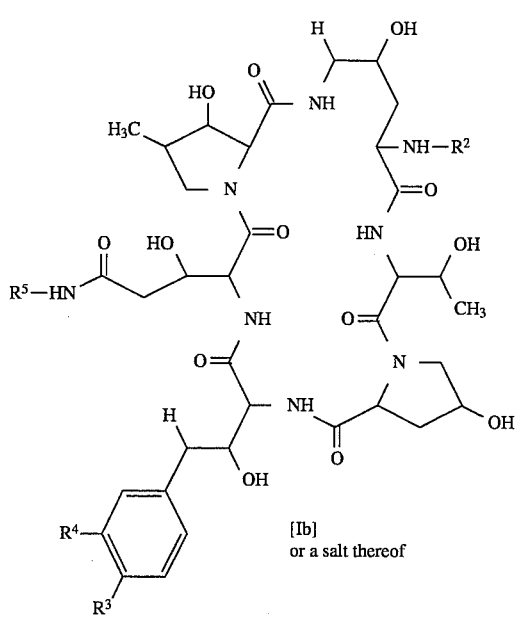
[Ib]
or a salt thereof
4
Process 3 -continued
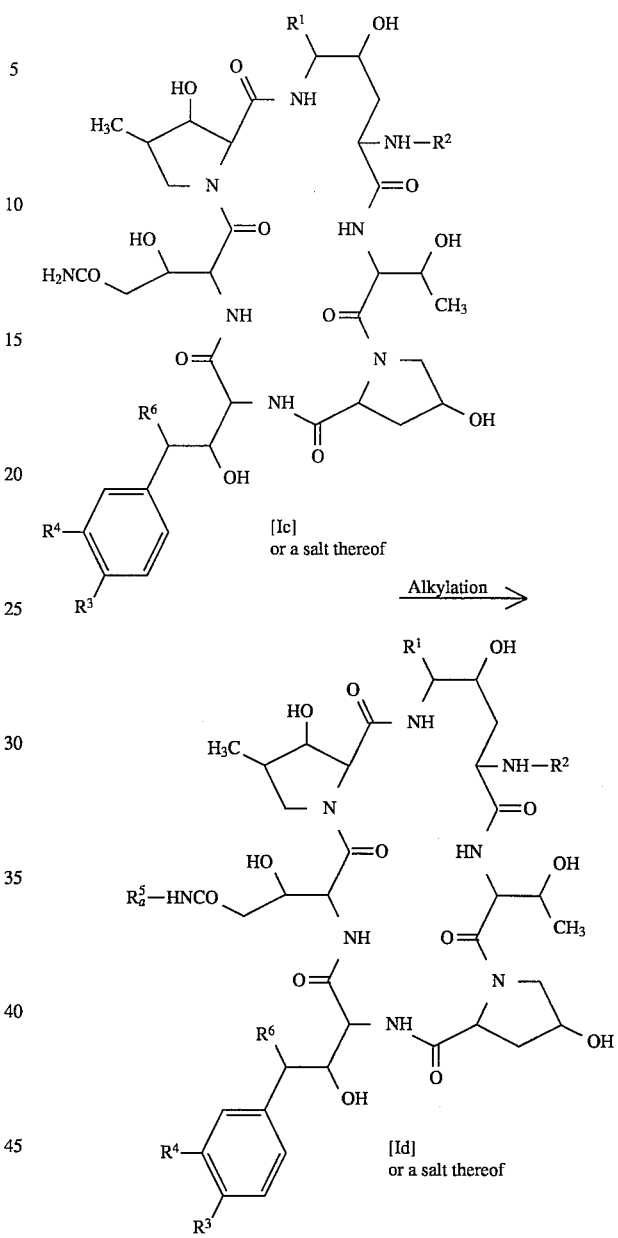
[Ic]
or a salt thereof
Alkylation →
[Id]
or a salt thereof 5,569,646
Process 4
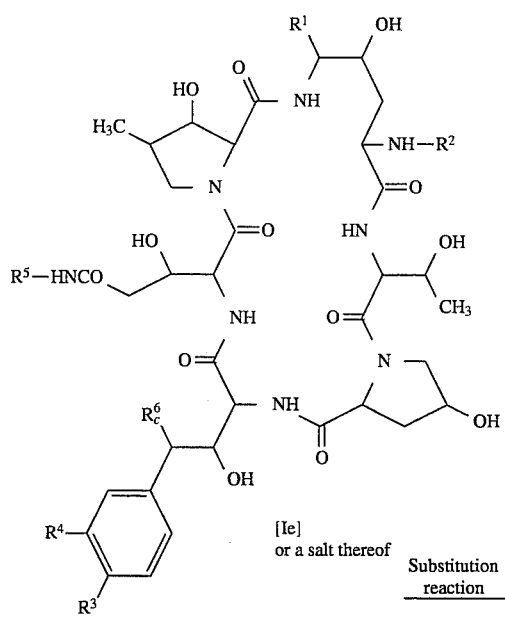
[Ie] or a salt thereof
Substitution reaction →
[If] or a salt thereof
Process 5
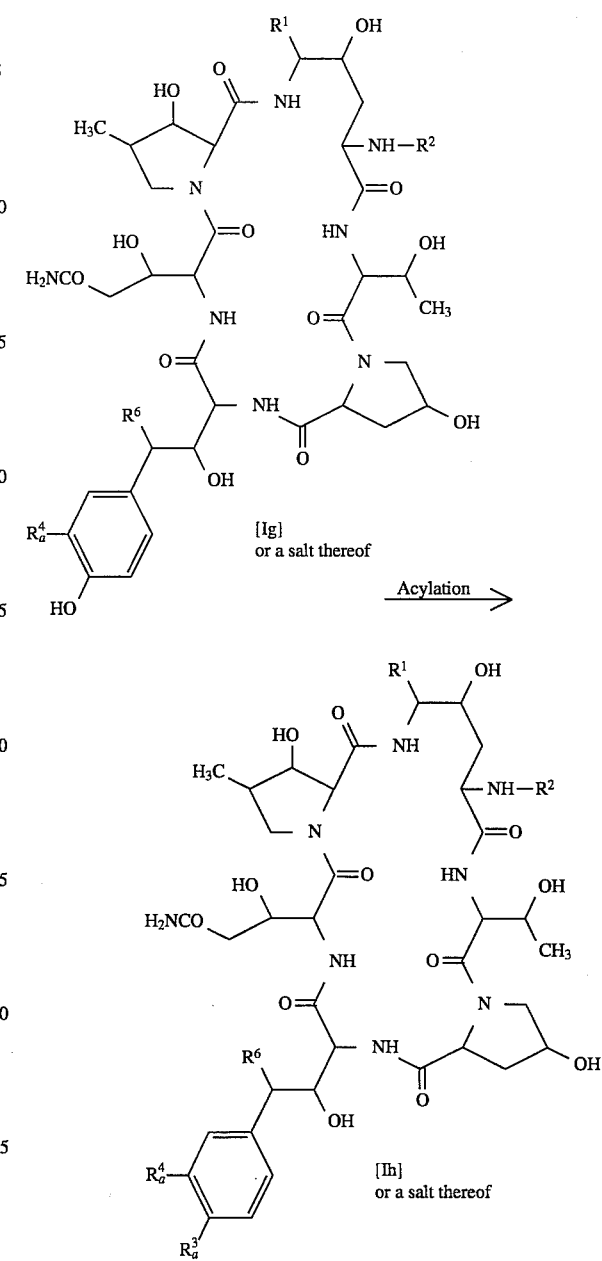
[Ig] or a salt thereof
Acylation →
[Ih] or a salt thereof Wherein $R^1$, $R^2$, $R^3$, $R^4$, $R^5$ and $R^6$ are each as defined above, $R_a^3$ is acyloxy, $R_a^4$ is hydroxysulfonyloxy, $R_a^5$ is lower alkyl which may have one or more suitable substituent(s), $R_a^6$ is hydroxy, or acyl (lower) alkylthio, $R_b^6$ is acyl (lower) alkylthio, $R_c^6$ is hydroxy.

Suitable pharmaceutically acceptable salts of the object compound [I] is conventional non-toxic mono or di salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydriodide, sulfate, phosphate, etc.], a salt with an amino acid [e.g. arginine, salt, aspartic acid salt, glutamic acid salt, etc.], and the like.

In the above and subsequent description of this specification, suitable examples of the various definitions are explained in detail as follows:

The term "lower" is intended to mean 1 to 6 carbon atom(s), preferably 1 to 4 carbon atom(s), unless otherwise indicated.

The term "higher" is intended to mean 7 to 20 carbon atoms, preferably 7 to 15 carbon atoms, more preferably 7 to 10 carbon atoms unless otherwise indicated.

Suitable "acyl group" and "acyl" moiety in the term "acyloxy" may be aliphatic acyl, aromatic acyl, heterocyclic acyl, arylaliphatie acyl and heterocyclic-aliphatic acyl derived from carboxylic acid, carbonic acid, carbamic acid, sulfonic acid, and the like.

Suitable example of the "acyl" moiety thus explained may be :lower alkanoyl [e.g. formyl, acetyl, propionyl, butyryl, isobutyryl, valeryl, hexanoyl, pivaloyl, etc.] which may have one or more (preferably 1 to 3) suitable substituent(s) such as halogen [e.g. fluoro, chloro, bromo, iodo]; aryl [e.g. phenyl, naphthyl, anthryl, etc.] which may have one or more (preferably 1 to 3) suitable substituent(s) like hydroxy, higher alkoxy as explained below, aforesaid aryl, or the like; lower alkoxy as explained below; amino; protected amino, preferably, acylamino such as lower alkoxycarbonylamino [e.g. methoxycarbonylamino, ethoxycarbonylamino, propoxycarbonylamino, butoxycarbonylamino, t-butoxycarbonylamino, pentyloxycarbonylamino, hexyloxycarbonylamino, etc.]; or the like; di (lower) alkylamino [e.g. dimethylamino, N-methylethylamino, diethylamino, N-propylbutylamino, dipentylamino, dihexylamino, etc.]; lower alkoxyimino [e.g. methoxyimino, ethoxyimino, propoxyimino, butoxyimino, t-butoxyimino, pentyloxyimino, hexyloxyimino, etc.]; ar (lower) alkoxyimino such as phenyl (lower) alkoxyimino [e.g. benzyloxyimino, phenethyloxyimino, benzhydryloxyimino, etc.] which may have one or more (preferably 1 to 3) suitable substituent(s) like higher alkoxy as explained below, or the like; heterocyclicthio, preferably, pyridylthio, which may have one or more (preferably 1 to 3) suitable substituent(s) like higher alkyl [e.g. heptyl, octyl, 2-ethylhexyl, nonyl, decyl, 3,7-dimethyloctyl, undecyl, dodecyl, tridecyl, tetradecyl, pentadecyl, 3-methyl-10-ethyldodecyl, hexadecyl, heptadecyl, octadecyl, nonadecyl, icosyl, etc.], or the like; heteromonocycyclic group [e.g. thienyl, imidazolyl, pyrazolyl, furyl, tetrazolyl, thiadiazolyl, etc.] which may have one or more (preferably 1 to 3) suitable substituent(s) like amino, aforesaid protected amino, aforesaid higher alkyl, or the like; or the like;

higher alkanoyl [e.g. heptanoyl, octanoyl, nonanoyl, decanoyl, undecanoyl, lauroyl, tridecanoyl, myristoyl, pentadecanoyl, palmitoyl, 10,12-dimethyltetradecanoyl, heptadecanoyl, stearoyl, nonadecanoyl, icosanoyl, etc.];

lower alkenoyl [e.g. acryloyl, methacryloyl, crotonoyl, 3-pentenoyl, 5-hexenoyl, etc.] which may have one or more (preferably 1 to 3) suitable substituent(s) such as aforesaid aryl which may have one or more (preferably 1 to 3) suitable substituent(s) like higher alkoxy as explained below, or the like, or the like;

higher alkenoyl [e.g. 4-heptenoyl, 3-octenoyl, 3,6-decadienoyl, 3,7,11-trimethyl-2,6,10-dodecatrienoyl, 4,10-heptadecadienoyl, etc.];

lower alkoxycarbonyl [e.g. methoxycarbonyl, ethoxycarbonyl, propoxycarbonyl, butoxycarbonyl, t-buroxycarbonyl, pentyloxycarbonyl, hexyloxycarbony, etc.]:

higher alkoxycarbonyl [e.g. heptyloxycarbonyl, octyloxycarbonyl, 2-ethylhexyloxycarbonyl, nonyloxycarbonyl, decyloxycarbonyl, 3,7-dimethyloctyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexadecyloxycarbonyl, heptadecyloxycarbonyl, octadecyloxycarbonyl, nonadecyloxycarbonyl, icosyloxycarbonyl, etc.];

aryloxycarbonyl [e.g. phenoxycarbonyl, naphthyloxycarbonyl, etc.];

arylglyoxyloyl [e.g. phenylglyoxyloyl, naphthylglyoxyloyl, etc.];

ar (lower) alkoxycarbonyl which may have one or more suitable substituent(s) such as phenyl (lower) alkoxycarbonyl which may have nitro or lower alkoxy [e.g, benzyloxycarbonyl, phenethyloxycarbonyl, p-nitrobenzyloxy carbonyl, p-methoxybenzyloxycarbonyl, etc,];

lower alkylsulfonyl [e.g. methylsulfonyl, ethylsulfonyl, propylsulfonyl, isopropylsulfonyl, pentylsulfonyl, butylsulfonyl, etc.]:

arylsulfonyl [e.g. phenylsulfonyl, naphthylsulfonyl, etc.] which may have one or more (preferably 1 to 3) suitable substituent(s) such as lower alkyl as explained below, higher alkoxy as explained below, or the like;

ar (lower) alkylsulfonyl such as phenyl (lower) alkylsulfonyl [e.g. benzylsulfonyl, phenethylsulfonyl, benzhydrylsulfonyl, etc.], or the like.

aroyl [e.g. benzoyl, naphthoyl, anthrylcarbonyl, etc.] which may have one or more (preferably 1 to 5) suitable substituent(s) such as aforesaid halogen; lower alkyl [e.g. methyl, ethyl, propyl, butyl, t-butyl, pentyl, hexyl, etc.]; aforesaid higher alkyl; lower alkoxy [e.g. methoxy, ethoxy, propoxy, butoxy, t-butoxy, pentyloxy, 4-methylpentyloxy, hexyloxy, etc.] which may have one or more (preferably 1 to 10) suitable substituent(s) like aforesaid lower alkoxy, aforesaid halogen, aforesaid aryl, or the like; higher alkoxy [e.g. heptyloxy, octyloxy, 2-ethylhexyloxy, nonyloxy, decyloxy, 8,7-dimethyloctyloxy, undecyloxy, dodecyloxy, tridecyloxy, tetradecyloxy, pentadecyloxy, 3-methyl-10-ethyldodecyloxy, hexadecyloxy, heptadecyloxy octadecyloxy, nonadecyloxy, icosyloxy, etc.] which may have one or more (preferably 1 to 17) suitable substituent(s) like aforesaid halogen; higher alkenyloxy [e.g. 3-heptenyloxy, 7-octenyloxy, 2,6-octadienyloxy, 5-nonenyloxy, 1-decenyloxy, 3,7-dimethyl-6-octenyloxy, 3,7-dimethyl-2,6-octadienyloxy, 8-undecenyloxy, 3,6,8-dodecatrienyloxy, 5-tridecenyloxy, 7-tetradecenyloxy, 1,8-pentadecadienyloxy, 15-hexadecenyloxy, 11-heptadecenyloxy, 7-octadecenyloxy, 10-nonadecenyloxy, 18-icosenyloxy, etc.]: carboxy; aforesaid aryl which may have one or more (preferably 1 to 3) suitable substituent(s) like aforesaid higher alkoxy, aryloxy [e.g. phenoxy, naphthyloxy, anthryloxy, etc.] which may have one more (preferably 1 to 3) suitable substituent(s) like aforesaid higher alkoxy; or the like; or the like.

In the "acyl group", the preferred one may be aroyl which may have one or more (preferably 1 to 5) suitable substituent(s) such as i) lower alkoxy, ii) higher alkoxy, or iii) aryl which may have one or more (preferably 1 to 3) lower alkoxy or higher alkoxy; in which the more preferred one may be benzoyl or naphthoyl, each of which may have 1 to 3 suitable substituent(s) selected from the group consisting of lower alkoxy, higher alkoxy and phenyl which may have 1 to 3 higher alkoxy, the much more preferred one may be benzoyl which may have 1 to 3 ($C_7$–$C_{16}$) alkoxy or phenyl which may have 1 to 3 ($C_5$–$C_{16}$) alkoxy; or naphthoyl which may have 1 to 3 ($C_7$–$C_{16}$) alkoxy, and the most preferred one may be 4-octyloxybenzoyl, 4-(4-heptyloxyphenyl)benzoyl, 6-heptyloxy-2-naphthoyl and 6-octyloxy-2-naphthoyl, 4-(4-pentyloxy phenyl)benzoyl, 4-(4-nonyloxyphenyl)benzoyl, 4-(4-methylpentyloxyphenyl)benzoyl, 6-(4-methylpentyloxy)-2-naphthoyl, 6-hexyloxy-2-naphthoyl, 4-(4-hexyloxyphenyl)benzoyl; and another preferred one may be aforesaid higher alkanoyl, in which the much more preferred one may be ($C_7$–$C_{17}$) alkanoyl, and the most preferred one may be palmitoyl.

The preferred "acyloxy" may be lower alkanoyloxy.

In the "acyl (lower) alkylthio", the preferred "acyl" moiety may be carboxy; or protected carboxy such as esterified carboxy [e.g. lower alkoxycarbonyl (e.g. methoxycarbonyl, ethoxycarbonyl, propoxycarbon, butoxycarbonyl, t-butoxycarbonyl, pentyloxycarbonyl, hexyloxycarbonyl, etc) etc]; in which the more preferred one may be carboxy.

Suitable "(lower) alkyl" moiety in the "acyl (lower) alkylthio" may be the ones as exemplified for "lower alkyl" in "lower alkyl which may have one or more suitable substituent(s)" before.

Suitable "lower alkyl" in "lower alkyl which may have one or more suitable substituent(s)" may include straight or branched ones having 1 to 6 carbon atom(s) such as methyl, ethyl, propyl, butyl, t-butyl, pentyl, hexyl, or the like, in which the preferred one may be ($C_1$–$C_6$) alkyl and the more preferred one may be methyl.

This "lower alkyl" may have one or more (preferably 1 to 3) suitable substituent(s) such as hydroxy, acyl [e.g. carboxy, protected carboxy {e.g. lower alkoxycarbonyl (e.g. methoxycarbonyl, ehoxycarbonyl, propoxycarbonyl, butoxycarbonyl, t-butoxycarbonyl, pentyloxycarbonyl, hexyloxycarbonyl, etc), etc}], di (lower) alkylamino [e.g. dimethylamino, diethylamino, N-methylethylamino, dipropylamino, dibutylamino, N-t-butylbutylamino, dipentylamino, dehexylamino, etc], cyclic amino, in which it may have the other hetero atom(s) in its ring member [e.g. 1-pyrrolidinyl, piperidino, 1-piperazinyl, morpholino, 1-pyridyl, dihydropyridin-1-yl, etc], or the like.

The preferred example of "lower alkyl which has one or more suitable substituent(s)" may include lower alkyl having hydroxy and carboxy, lower alkyl having di (lower) alkylamino; and lower alkyl having cyclic amino, in which the more preferred one may include ($C_1$–$C_4$) alkyl having hydroxy and carboxy; ($C_1$–$C_4$) alkyl having di ($C_1$–$C_4$) alkylamino; and ($C_1$–$C_4$) alkyl having piperidino, and the most preferred one may be 1-hydroxy-1-carboxymethyl, dimethylaminomethyl and piperidinomethyl.

In the compound (I) as explained above, (1) the preferred one is the compound wherein $R^1$ is hydrogen, $R^2$ is aroyl which may have one or more suitable substituent(s) selected from the group consisting of i) lower alkoxy, ii) higher alkoxy and iii) aryl which may have one or more lower alkoxy or higher alkoxy; or higher alkanoyl;

$R^3$ is hydroxy or acyloxy, $R^4$ is hydroxy or hydroxysulfonyloxy, $R^5$ is hydrogen or lower alkyl which may have one or more suitable subtituent (s) selected from the group consisting of hydroxy, acyl, di (lower) alkylamino and cyclic amino, and $R^6$ is hydrogen, hydroxy or acyl (lower) alkylthio, and (2) the more preferred one is the compound wherein $R^2$ is benzoyl or naphthoyl, each of which may have 1 to 3 suitable substituent(s) selected from the group consisting of lower alkoxy; higher alkoxy; and phenyl which may have 1 to 3 higher alkoxy, $R^3$ is hydroxy, $R^5$ is hydrogen, and $R^6$ is hydrogen or hydroxy, $R^1$ and $R^4$ are each as defined above, and (3) the much more preferred one is the compound wherein $R^2$ is benzoyl having higher alkoxy, benzoyl having phenyl which has higher alkoxy, naphthoyl having lower alkoxy, or naphthoyl having higher alkoxy, and $R^6$ is hydrogen, $R^1$, $R^3$, $R^4$ and $R^5$ are each as defined in (2) and (4) the still more preferred one may be i) the compound wherein $R^2$ is benzoyl having higher alkoxy, $R^1$, $R^3$, $R^4$, $R^5$ and $R^6$ are each as defined in (3), or ii) the compound wherein $R^2$ is benzoyl having phenyl which has higher alkoxy, $R^1$, $R^3$, $R^4$, $R^5$ and $R^6$ are each as defined in (3), or iii) the compound wherein $R^2$ is naphthoyl having lower alkoxy, $R^1$, $R^3$, $R^4$, $R^5$ and $R^6$ are each as defined in (3), or iv) the compound wherein $R^2$ is naphthoyl having higher alkoxy, $R^1$, $R^3$, $R^4$, $R^5$ and $R^6$ are each as defined in (3), and (5) another much more preferred one is the compound wherein $R^1$ is hydrogen, $R^2$ is benzoyl having higher alkoxy, benzoyl having phenyl which has higher alkoxy, naphthoyl having lower alkoxy, or naphthoyl having higher alkoxy, $R^3$ is hydroxy, $R^4$ is hydroxy or hydroxysulfonyloxy, $R^5$ is hydrogen, and $R^6$ is hydroxy, and (6) another still more preferred one may be i) the compound wherein $R^2$ is benzoyl having higher alkoxy, $R^1$, $R^3$, $R^4$, $R^5$ and $R^6$ are each as defined in (5), or ii) the compound wherein R² is benzoyl having phenyl which has higher alkoxy, R¹, R³, R⁴, R⁵ and R⁶ are each as defined in (5), or iii) the compound wherein R² is naphthoyl having lower alkoxy, R¹, R³, R⁴, R⁵ and R⁶ are each as defined in (5), or iv) the compound wherein R² is naphthoyl having higher alkoxy, R¹, R³, R⁴, R⁵ and R⁶ are each as defined in (5).

The processes for preparing the object compound [I] or a salt thereof the present invention are explained in detail in the following.

Process 1

The object compound [I] or its salt can be prepared by reducing a compound [II] or its salt.

Suitable salts of the compounds [I] and [II] may be the same as those exemplified for the compound [I].

The reaction can be carried out in a conventional manner, namely, chemical reduction or catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, hydride transfer reagent such as aluminum hydride compound (e.g. lithium aluminum hydride, lithium hydridotri-t-butoxyaluminate, etc.), borohydride compound (e.g. sodium borohydride, sodium cyanoborohydride, etc.) or the like etc.].

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.] or the like.

The reaction of this process is usually carried out in a solvent such as water, alcohol [e.g. methanol, ethanol, propanol, etc.], acetic acid, diethyl ether, dioxane, tetrahydrofuran, methylene chloride, etc. or a mixture thereof.

The reaction is preferably carried out under somewhat milder conditions such as under cooling to warming.

It is included within the scope of the present invention that "hydroxy" in $R_a^6$ may be reduced to "hydrogen" during the reaction.

Process 2

The object compound [Ib] or a salt thereof can be prepared by reducing the compound [Ia] or a salt thereof to reduction reaction.

This reaction can be carried out in substantially the same manner as Process 1, and therefore the reaction mode and reaction conditions [e.g. solvent, reaction temperature, etc.] of this reaction are to be referred to those as explained in Process 1.

Process 3

The object compound [Id] or a salt thereof can be prepared by subjecting the compound [Ic] or a salt thereof to alkylation reaction.

Suitable agent for this alkylation reaction may include 1) lower alkanal [e.g. formaldehyde, ethanal, propanal, butanal, t-butanal, pentanal, hexanal, etc.] which may have one or more (preferably 1 to 3) suitable substituent(s) as exemplified for the substituent(s) of "lower alkyl (which may have one or more suitable substituent(s). 2) a compound of the formula:

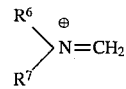

(wherein R⁶ and R⁷ are each lower alkyl as exemplified before), 3) a compound of the formula:

[wherein a group of the formula:

is cyclic aminium group, in which it may have the other hetero atom(s) in its ring member (e.g. pyrrolidinium, piperidinium, piperadinium, morpholinium, etc)], and the like.

This reaction is usually carried out in a conventional solvent which does not adversely influence the reaction such as water, alcohol [e.g. methanol, ethanol, propanol, etc.], tetrahydrofuran, dioxane, dimethyl sulfoxide, N,N-dimethylformamide, acetone, or a mixture thereof.

The reaction temperature is not critical, and the reaction is usually carried out under cooling to warming.

Process 4

The object compound [If] or a salt thereof can be prepared by subjecting the compound [Ie] or a salt thereof to substitution reaction with acyl (lower) alkylthiol.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvents which do not adversely affect the reaction, or the mixture thereof.

The reaction temperature is not critical and the reaction is usually carried out under cooling to heating.

The reaction is usually carried out in the presence of an acid including Lewis acid.

Suitable acid may include an organic [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, zinc halide (e.g. zinc chloride, zinc bromide, etc.), etc.] and the like.

When the acid and/or the starting compound are in liquid, they can be used also as a solvent.

Process 5

The object compound [Ih] or a salt thereof can be prepared by subjecting the compound [Ig] or a salt thereof to acylation reaction.

Suitable acylating agent to be used in the present acylation reaction may include the compound of the formula:

$$R_b^3\text{—OH} \qquad [\text{III}]$$

[wherein $R_b^3$ is lower alkanoyl] or its reactive derivative or a salt thereof.

Suitable "lower alkanoyl" in the compound [III] may include the ones as exemplified for "lower alkanoyl" moiety in "lower alkanoyloxy" before.

Suitable reactive derivative at the carboxy group of the compound [III] may include an acid halide, an acid anhydride, an activated amide, an activated ester, and the like. Suitable examples of the reactive derivatives may be an acid chloride; an acid azide; a mixed acid anhydride with an acid such as substired phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivaric acid, pentanoic acid, isopentanoic acid, 2-ethylbutyric acid, trichloroacetic acid, etc.]; or aromatic carboxylic acid [e.g. benzoic acid, etc.]; a symmetrical acid anhydride [e.g. acetic anhydride, etc.], an activated amide with imidazole, 4-substituted imidazole, dimethylpyrazole, triazole, tetrazole or 1-hydroxy -1H-benzotriazole; or an activated ester [e.g. cyanomethyl ester, methoxymethyl ester, dimethyliminomethyl $[[CH_3]_2N^+$ $=CH—]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-[1H]-pyridone, N-hydroxysuccinimide, N-hydroxyphthalimide, 1-hydroxy-1H-benzotriazole, etc.], and the like. These reactive derivatives can optionally be selected from them according to the kind of the compound [III] to be used.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction, These conventional solvent may also be used in a mixture with water.

In this reaction, when the compound [III] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl) carbadiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro- 1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc,; or the like.

The reaction may also be carried out in the presence of an inorganic or organic base such as an alkali metal carbonate, alkali metal bicarbonate, tri (lower) alkylamine [e.g. triethylamine, etc.], pyridine, di (lower) alkylaminopyridine [e.g. 4-dimethylaminopyridine, ], N-(lower) alkylmorpholine, N,N-di (lower) alkylbenzylamine, or the like.

The reaction temperature is not critical, and the reaction is usually carried out under cooling to warming.

The starting compounds [II] can be prepared by the fermentation and synthetic processes disclosed in EP 0462531 A2 and the Preparations in this specification.

A culture of Coleophoma sp. F-11899, which is used in said fermentation process, has been deposited with the Fermentation Research Institute Agency of Industrial Science and Technology (1-3, Higashi 1 chome, Tsukuba-shi, IBARAKI 305 JAPAN) on Oct. 26, 1989 under the number of FERM BP-2635.

Biological property of the polypeptide compound [I] of the present invention

In order to show the usefulness of the polypeptide compound [I] of the present invention, the biological data of the representative compound is explained in the following.

Test A (Antimicrobial activity):

In vitro antimicrobial activity of the compound of Example 19 (Major Compounds) disclosed later were determined by the two-fold agar-plate dilution method as described below.

Test Method

One loopful of an overnight culture of each test microorganism in Sabouraud broth containing 2% Glucose ($10^5$ viable cells per ml) was streaked on yeast nitrogen base dextrose agar (YNBDA) containing graded concentrations of the compound [I], and the minimal inhibitory concentration (MIC) was expressed in terms of µg/ml after incubation at 30° C. for 24 hours.

Test Result

| | MIC (µg/ml) |
|---|---|
| Test organism | Test Copound The compound of Example 19 (Major Compound) |
| *Candida albicans* YU - 1200 | 0.05 |

From the test result, it is realized that the polypeptide compound [I] of the present invention has an antimicrobial activity (espesially, antifungal activity).

The pharmaceutical composition of this invention can be used in the form of a pharmaceutical preparation, for example, in solid semisolid or liquid form, which contains the polypeptide compound [I] or a pharmaceutically acceptable salt thereof, as an active ingredient in admixture with an organic or inorganic carrier, or excipient suitable for rectal, pulmonary (nasal or buccal inhalation), nasal, ocular, external (topical), oral, or parenteral (including subcutaneous, intravenous and intramuscular) administration or insufflation. The active ingredient may be compound, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, If necessary, in addition, auxiliary, stabilizing, thickening and coloring agents and perfumes may be used. The polypeptide compound [I] or a pharmaceutically acceptable salt thereof is/are included in the pharmaceutical composition in an amount sufficient to produce the desired antimicrobial effect upon the process or condition of diseases. For applying the composition to human, it is preferable to apply it by intravenous, intramuscular, pulmonary, or oral administration, or insufflation. While the dosage of therapeutically effective amount of the polypeptide compound [I] varies from and also depends upon the age and condition of each individual patient to be treated, in the case of intravenous administration, a daily dose of 0.01–20 mg of the polypeptide compound [I] per kg weight of human being in the case of intramuscular administration, a daily dose of 0.1–20 mg of the polypeptide compound [I] per kg weight of human being, in case of oral administration, a daily dose of 0.5–50 mg of the polypetide compound [I] per kg weight of human being is generally given for treating or preventing infectious diseases.

Especially in case of the treatment or prevention of *Pneumocystis carinii* infection, the followings are to be noted.

For administration by inhalation, the compounds of the present invention are conveniently delivered in the form of an aerosol spray presentation from pressurized as powders which may be formulated and the powder compositions may be inhaled with the aid of an insufflation powder inhaler device. The preferred delivery system for inhalation is a metered dose inhalation aerosol, which may be formulated as a suspension or solution of compound in suitable propellants such as fluorocarbons or hydrocarbons.

Because of desirability to directly treat lung and bronchi, aerosol adminisration is a preferred method of administration. Insufflation is also a desirable method, especially where infection may have spread to ears and other body cavities.

Alternatively, parenteral administration may be employed using drip intravenous administration.

The following Preparations and Examples are given for the purpose of illustrating the present invention in more detail.

Preparation 1

To a solution of methyltrichlorosilane (0.82 ml) in acetonitrile was added 1-ethoxymethylpiperidine (1 g) under ice-cooling and stirred for five minutes at the same temperature. Diethyl ether was added thereto and the produced precipitate was collected by filtration and dried to give 1-methylenepiperidinium chloride (0.88 g).

IR (Nujol): 3100, 2700, 1420, 1110, 920 cm$^{-1}$ EI-MS: e/z=133 (M+)

Preparation 2

A solution of 6-hydroxy-2-naphthoic acid (1.04 g) in a mixture of 10% sodium hydroxide aqueous solution (4.44 ml) and dimethyl sulfoxide (18 ml) was stirred for half an hour at 80° C. Then heptyl bromide (0.872 ml) was added thereto and stirred for 5 hours at 60° C. The reaction mixture was added to water (50 ml) and the mixture was adjusted to pH 3 with conc. hydrochloric acid. The resultant precipitate was collected by filtration and dried to give 6-heptyloxy-2-naphthoic acid (1.39 g).

IR (Nujol): 1660, 1620, 1210 cm$^{-1}$ NMR (DMSO-$d_6$, δ): 0.88 (3H, t, J=6.6 Hz), 1.2–1.6 (8H, m), 1.7–1.9 (2H, m), 4.10 (2H, t, J=6.5 Hz), 7.18 (1H, dd, J=8.9 Hz and 2.4 Hz), 7.35 (1H, d, J=2.4 Hz), 7.79 (1H, d, J=8.6 Hz), 7.9–8.1 (2H, m), 8.45 (1H, s)

Preparation 3

The following compound was obtained according to a similar manner to that of Preparation 2. 4-(4-pentyloxyphenyl)benzoic acid IR(KBr): 1678, 1605, 1200, 833 cm$^{-1}$ Preparation 4

The following compound was obtained according to a similar manner to that of Preparation 2. 4-(4-nonyloxyphenyl)benzoic acid IR(Nujol): 1686, 1604, 1203, 837 cm$^{-1}$ Preparation 5

The following compound was obtained according to a similar manner to that of Preparation 2. 6-(4-methylpentyloxy)-2-naphthoic acid IR(KBr): 1674, 1624, 1292, 1213 cm$^{-1}$ NMR (CDCl$_3$, δ): 0.64(6H, d, J=6.6 Hz), 1.3–1.5(2H, m), 1.65(1H, m), 1.7–2.0(2H, m), 4.08(2H, t, J=6.6 Hz), 7.15(1H, d, J=2.3 Hz), 7.21 (1H, dd, J=2.3 and 8.9 Hz), 7.76(1H, d, J=8.7 Hz), 7.87(1H, d, J=8.9 Hz), 8.08(1H, dd, J=2.3 and 8.7 Hz), 8.63(1H, s)

Preparation 6

To a susupension of N-hydroxysuccinimide (0.56 g) and 6-heptyloxy-2-naphthoic acid (1.39 g) in methylene chloride (42 ml) was added 1-ethyl-3-(3-dimethylaminopropyl)carbodiimide hydrochloride (1.21 g) and stirred for 3 hours at room temparature. The reaction mixture was added to water (100 ml). The organic layer was separated and dried over magnesium sulfate. Magnesium sulfate was filtered off, and the filtrate was evaporated under reduced pressure to give succinimido 6-heptyloxy-2-naphthoate (1.48 g).

IR (Nujol): 1760, 1740, 1620 cm$^{-1}$ NMR (CDCl$_3$, δ): 0.91 (3H, t, J=6.6 Hz), 1.2–1.6 (8H, m), 1.7–2.0 (2H, m), 2.93 (4H, s), 4.10 (2H, t, J=6.5 Hz), 7.1–7.3 (2H, m), 7.77 (1H, d, J=8.6 Hz), 7.84 (1H, d, J=8.6 Hz), 8.03 (1H, dd, J=8.9 Hz and 2.4 Hz), 8.65 (1H, s)

Preparation 7

The following compound was obtained according to a similar manner to that of Preparation 6. 1-[4-(4-pentyloxyphenyl)benzoyl[1H-benzotriazole-3-oxide IR(KBr): 1776, 1605, 1194, 985 cm$^{-1}$ NMR (CDCl$_3$, δ): 0.96(3H, t, J=7.0 Hz), 1.3–1.6(4 H, m), 1.84(2H, quint, J=6.8 Hz), 4.03(2H, t, J=6.5 Hz), 7.03(2H, d, J=8.7 Hz), 7.35–7.68(3H, m), 7.63(2H, d, J=8.7 Hz), 7.79(2H, d, J=8.4 Hz), 8.12 (1H, d, J=8.2 Hz), 8.32(2H, d, J=8.4)

Preparation 8

The following compound was obtained according to a similar manner to that of Preparation 6. 1-[4-(4-nonyloxyphenyl)benzoyl]-1H-benzotriazole-3-oxide IR(KBr): 1774, 1600 cm$^{-1}$ NMR (CDCl$_3$, δ): 0.89 (3H, t,J=6.8 Hz), 1.1–1.6 (12H,m), 1.83 (2H,quint, J=6.5 Hz), 4.03 (2H,t,J=6.5 Hz), 7.03 (2H,d,J=8.8 Hz), 7.35–7.68 (3H, m), 7.64 (2H,d,J=6.8 Hz), 7.79 (2H,d,J=6.8 Hz), 8.12 (1H, d,J=9.2 Hz), 8.32 (2H,d,J=6.8 Hz)

Preparation 9

The following compound was obtained according to a similar manner to that of Preparation 6. 1-[6-(4-methylpentyloxy)-2-naphthoyl]-1H-benzotriazole-3-oxide IR(KBr): 1784, 1628, 1196 cm$^{-1}$ The Starting Compounds used and the Object Compounds obtained in the following Preparations and Examples are given in the table as below, in which the formula of the starting compounds are in the upper column and the formula of the object compounds are in the lower column, respectively.

| Formula |
|---|
| Preparation No. |
10
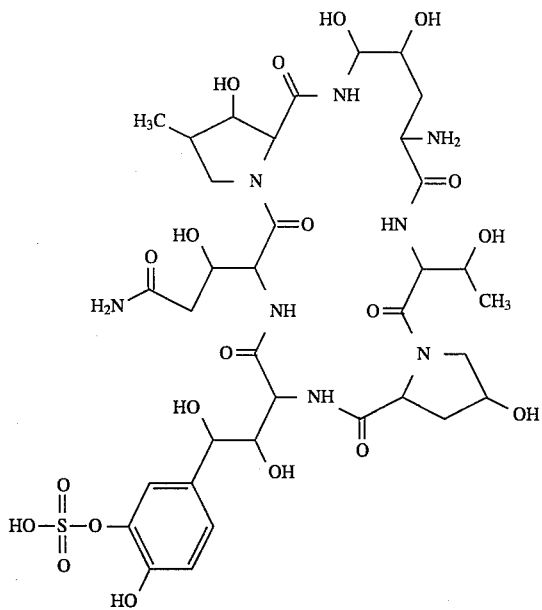
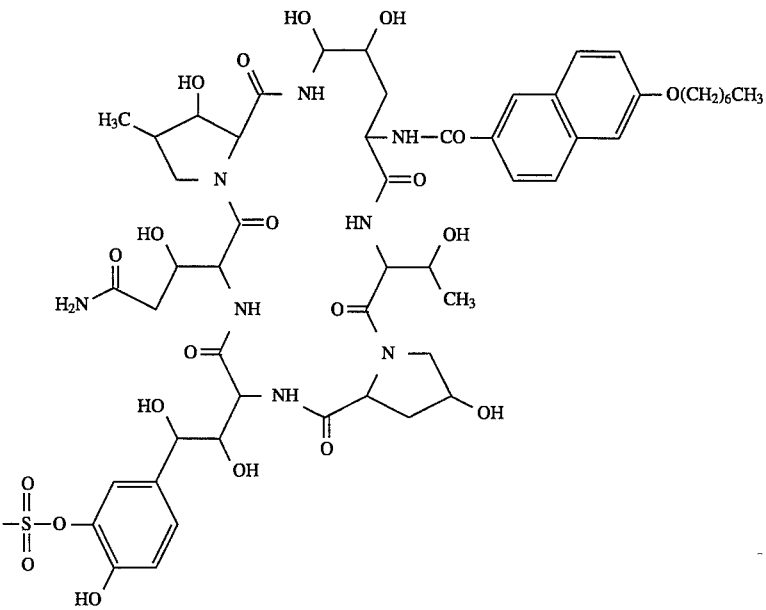

| Formula |
|---|
| 11 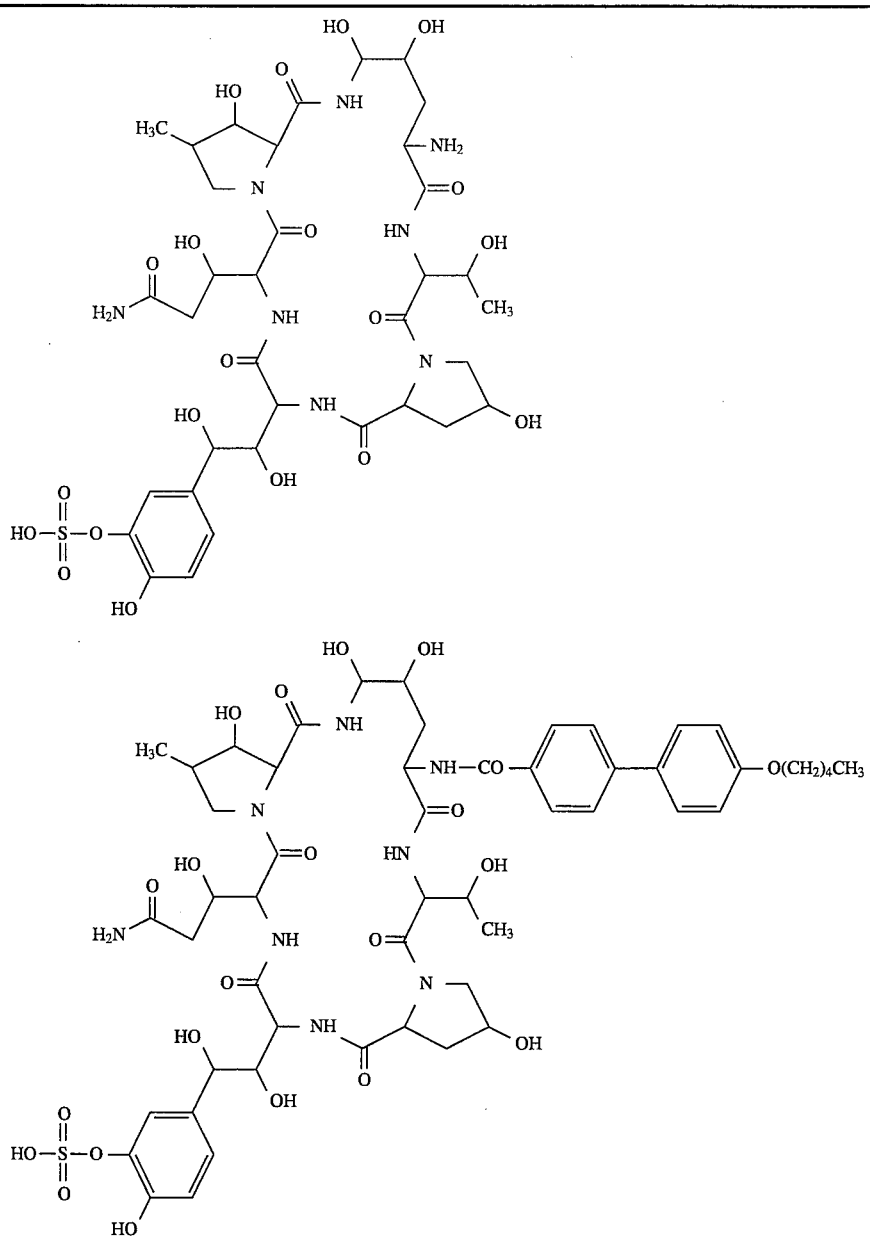 |

| Formula |
|---|
| 12 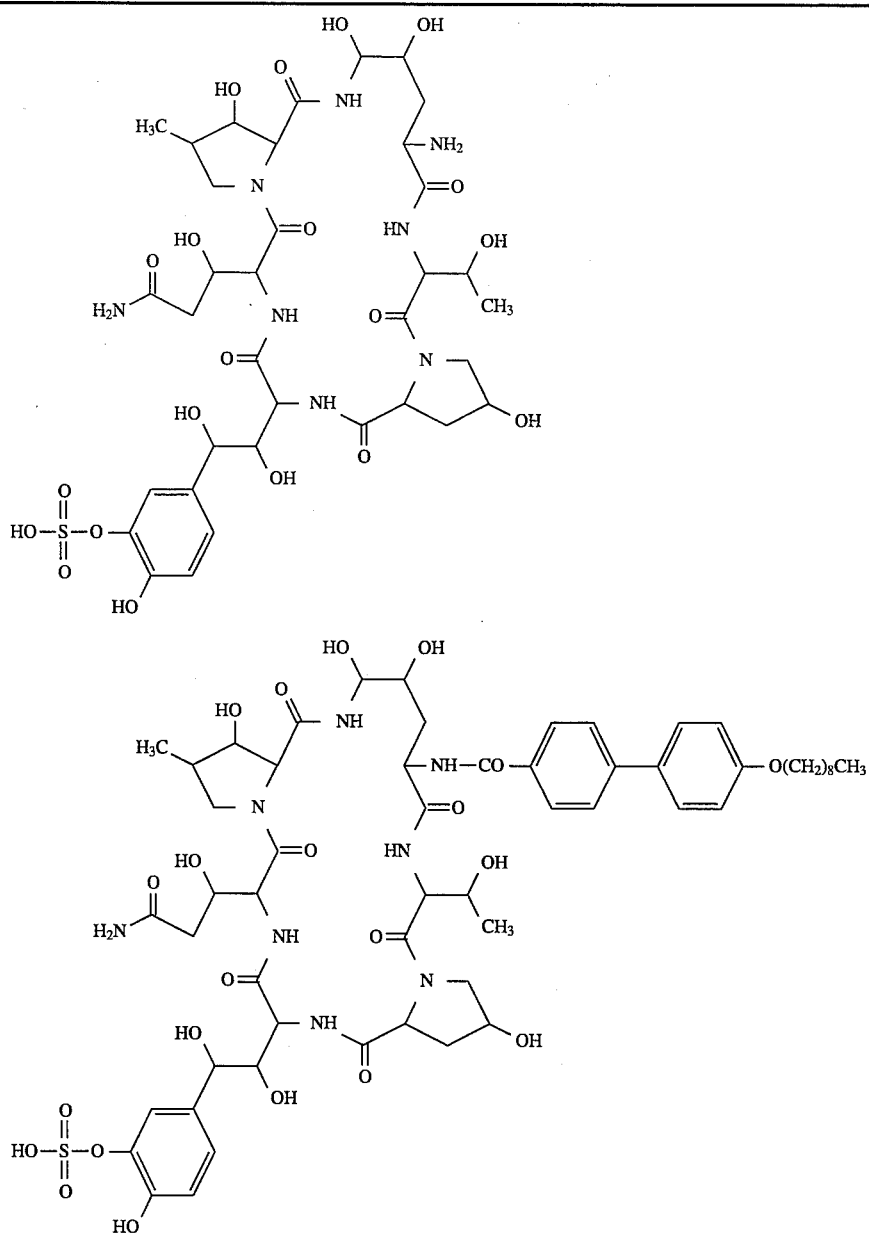 |

-continued
| Formula |
|---|
| 13 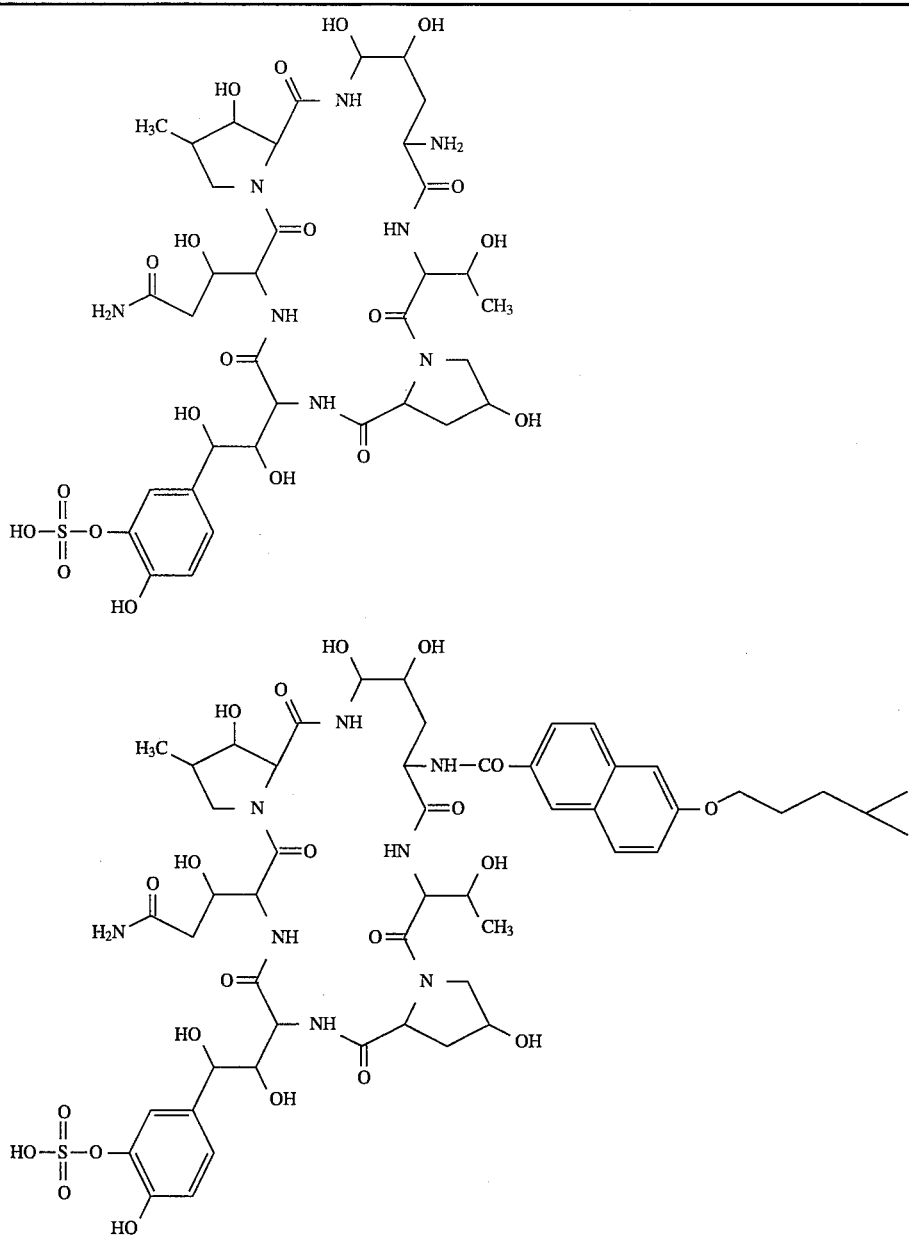 |

Formula
14
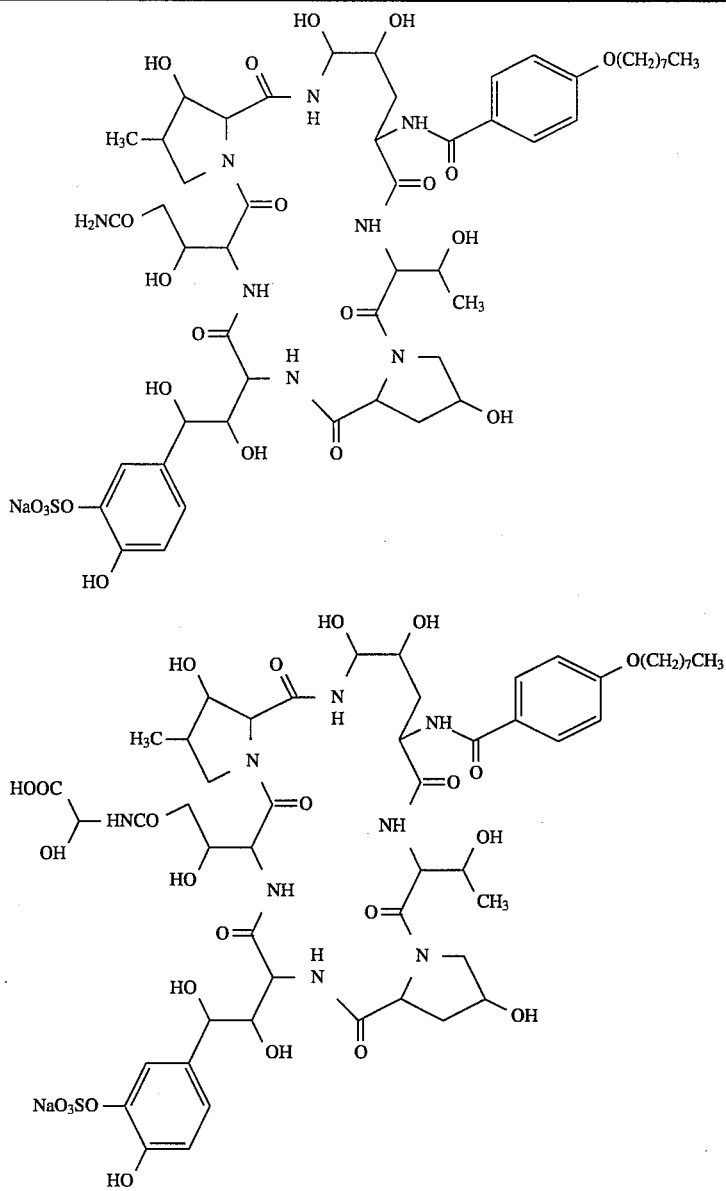

-continued
Formula
15
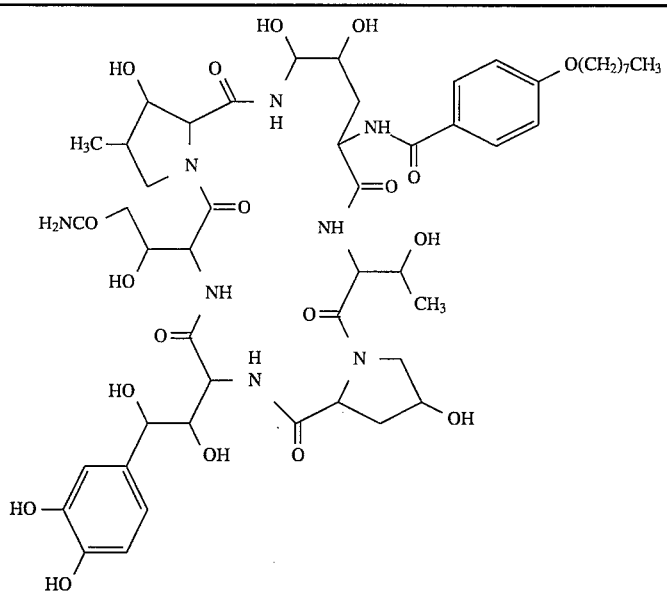
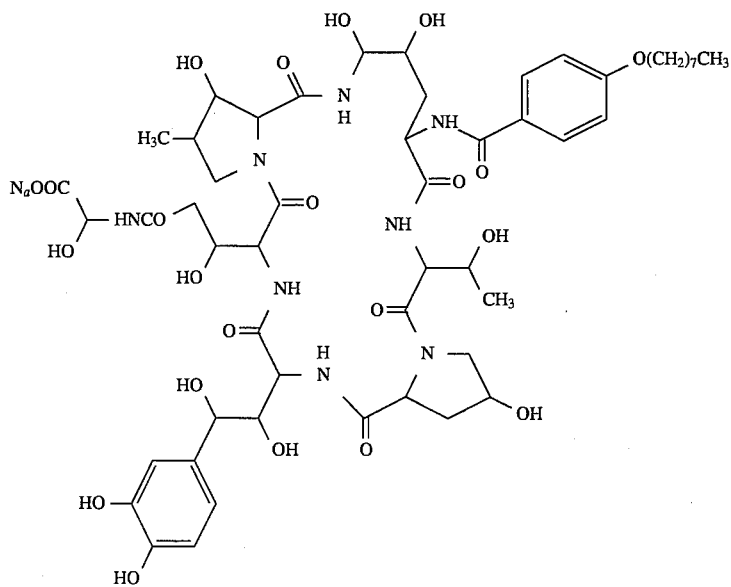

Formula
16
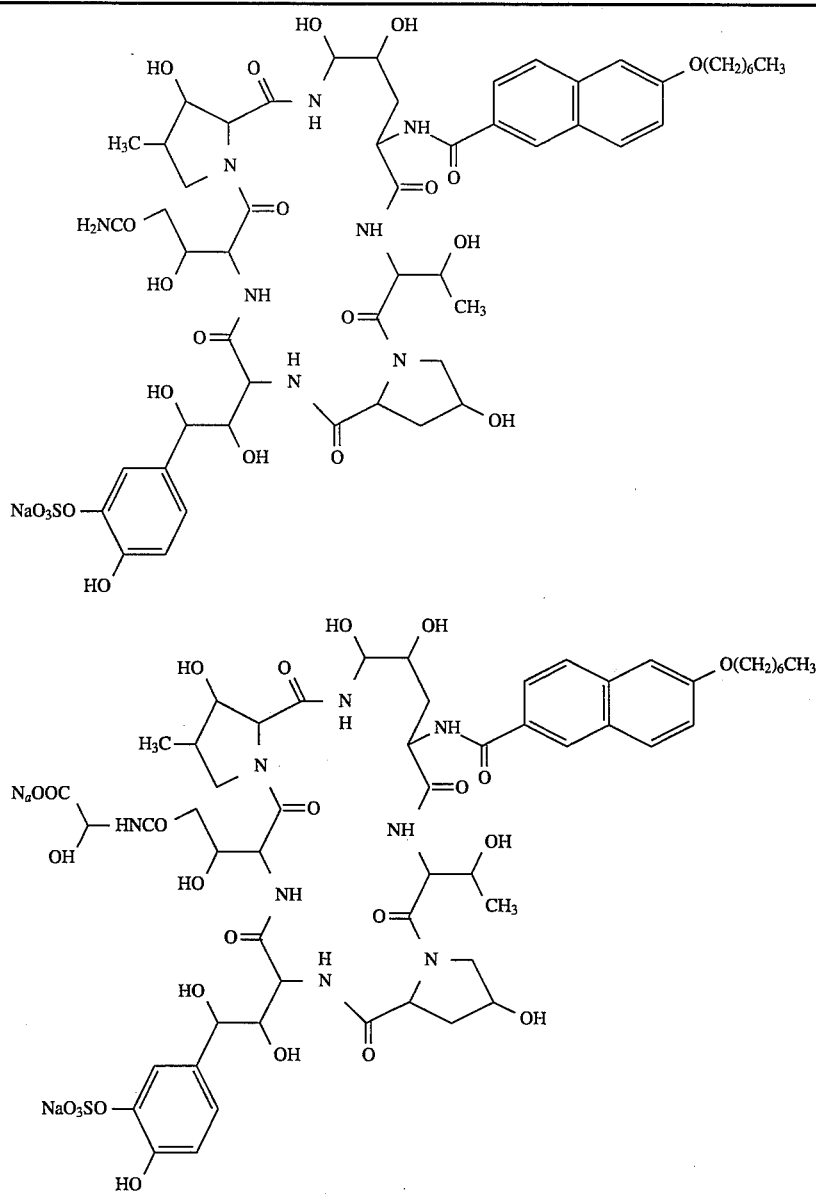

| Formula |
|---|
| 17 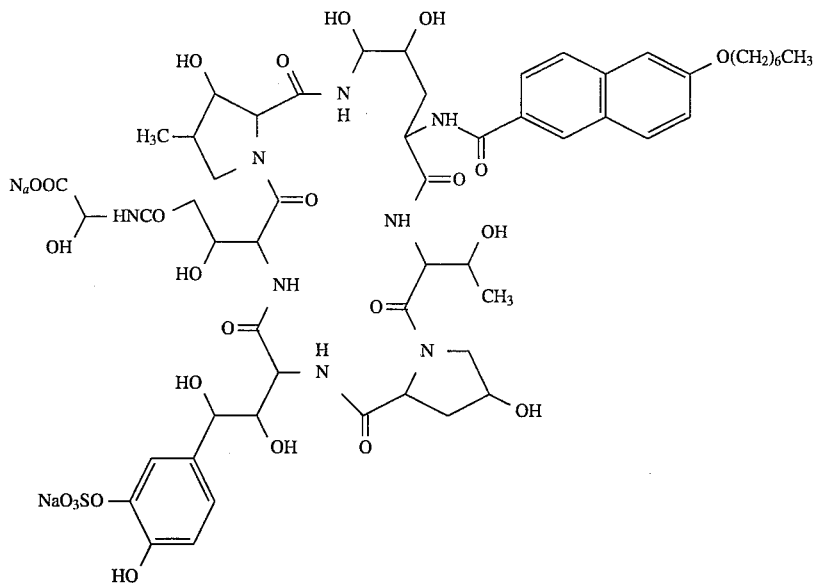 |

-continued
| Formula |
|---|
| Example No. |
| 1 |
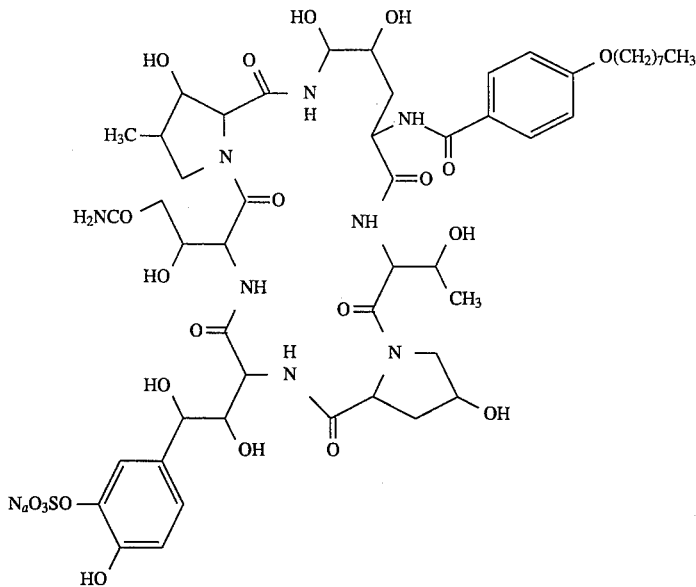
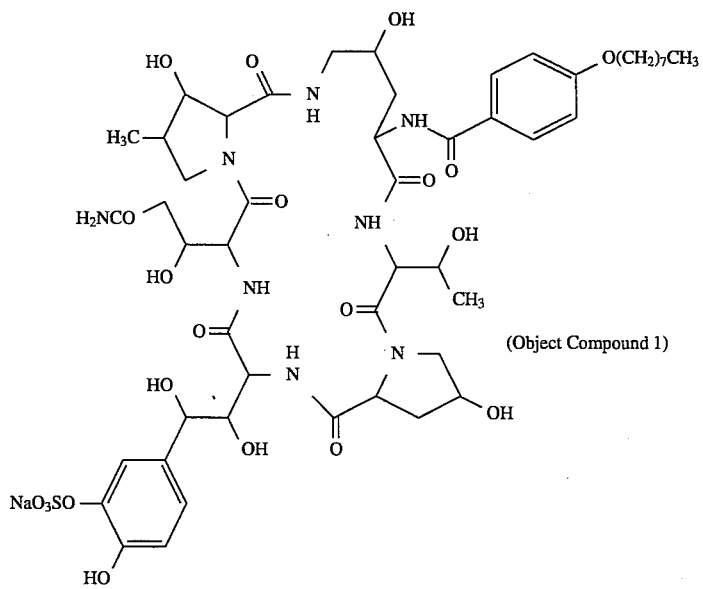
(Object Compound 1)

-continued
| Formula |
|---|
| 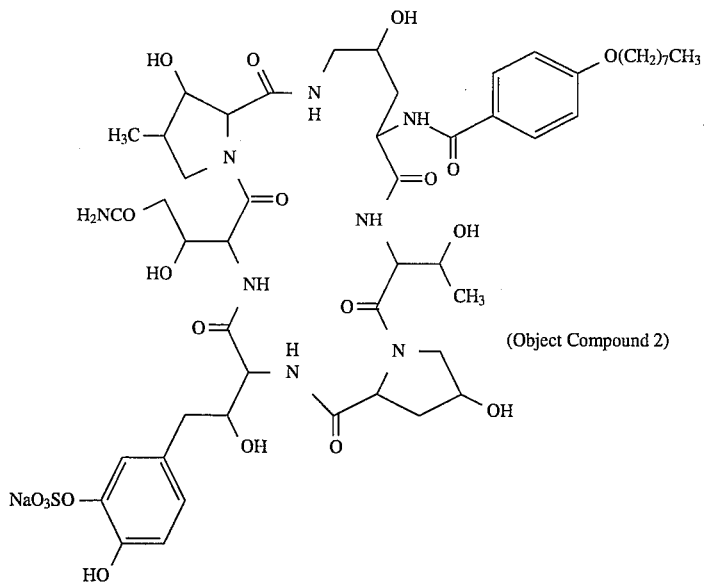 (Object Compound 2) |
| 2 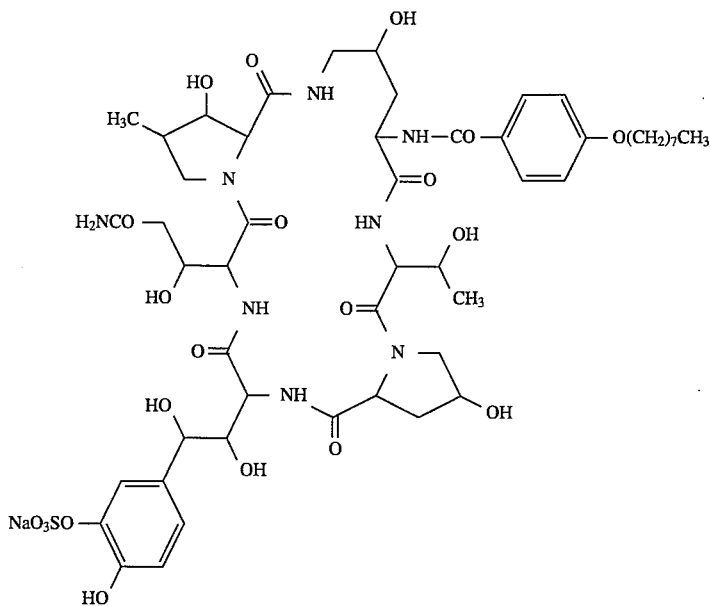 |

| Formula |
|---|
| 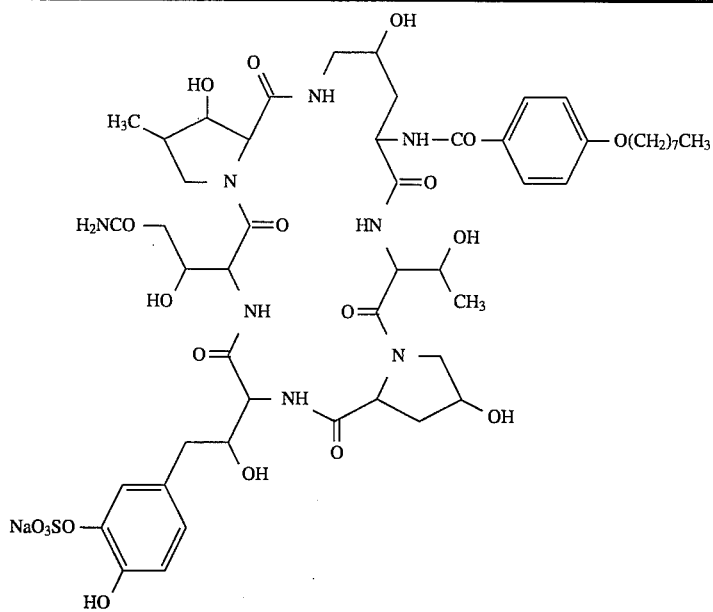 |
| 3 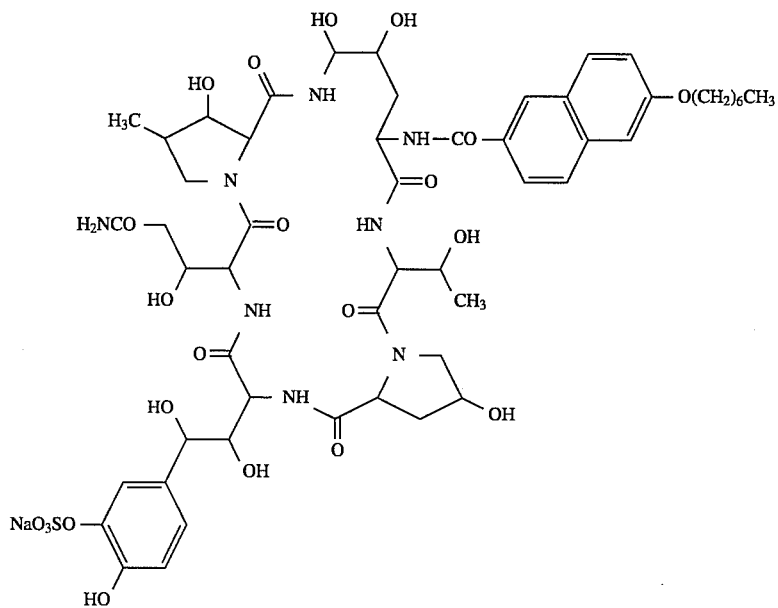 |

-continued
Formula
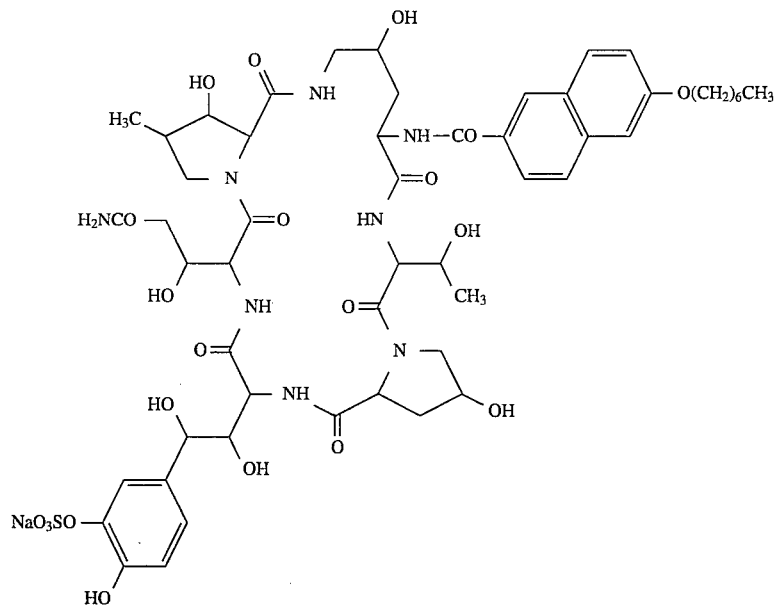
4
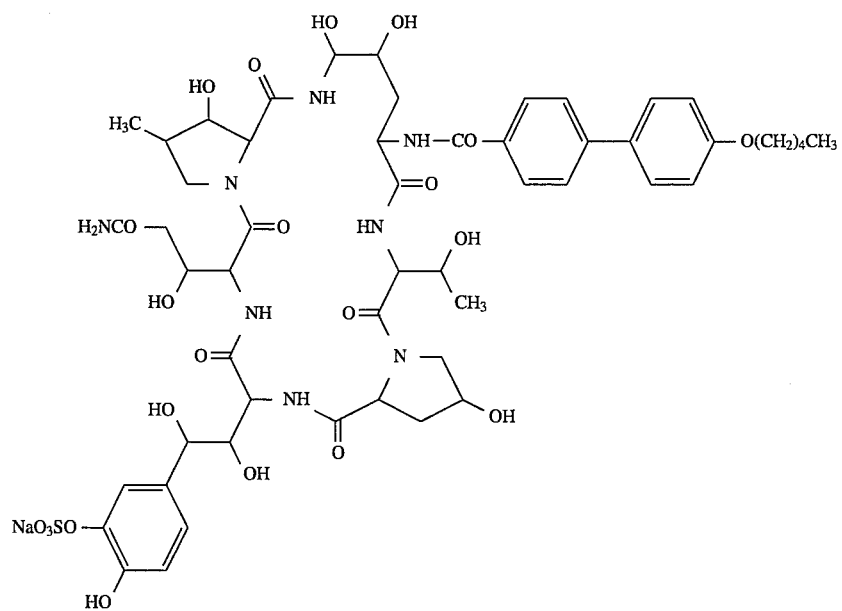

5,569,646
-continued
| Formula |
|---|
| 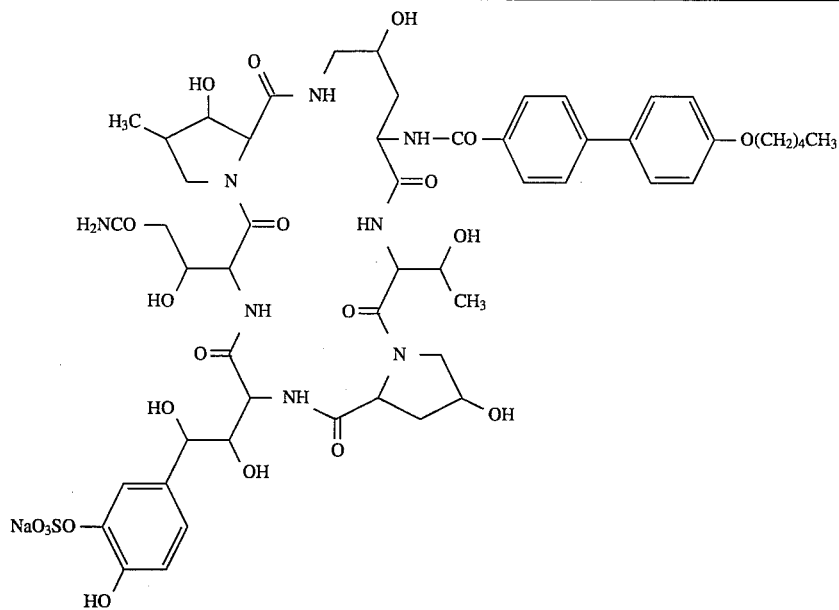 |
| 5 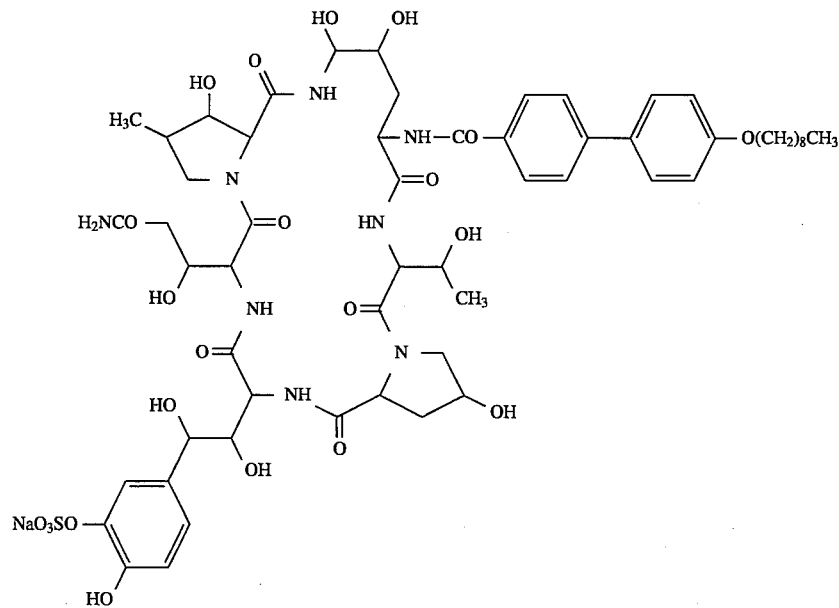 |

| Formula |
|---|
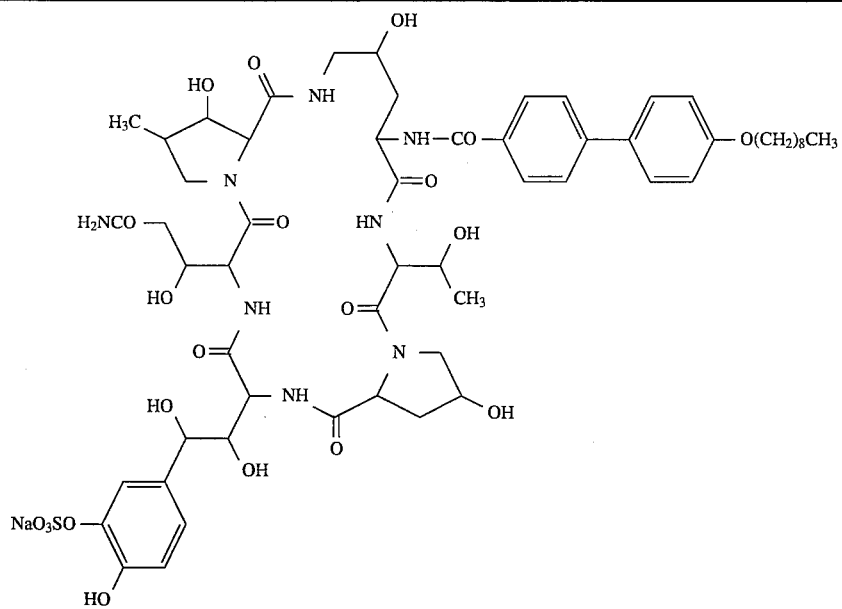
6
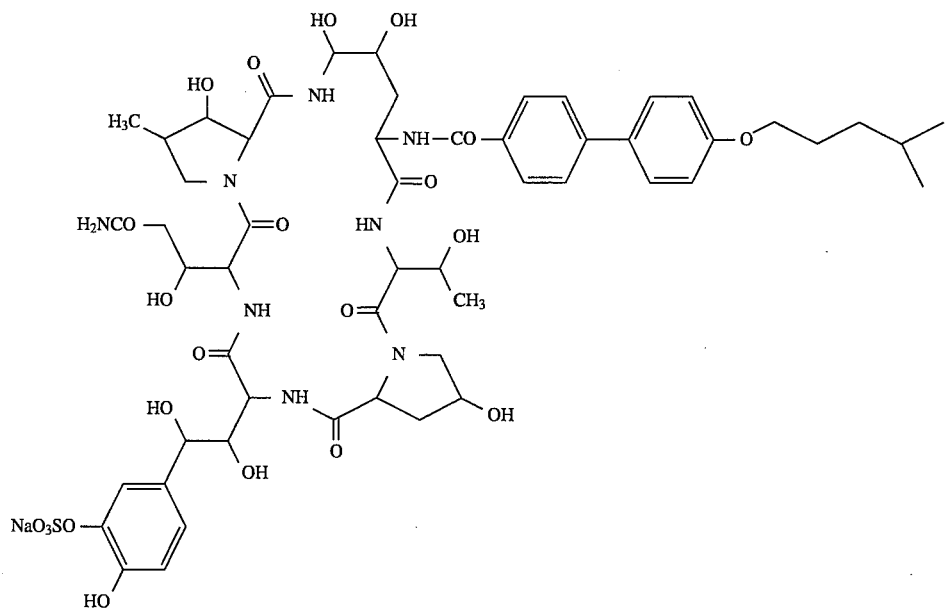

5,569,646
| Formula |
|---|
| 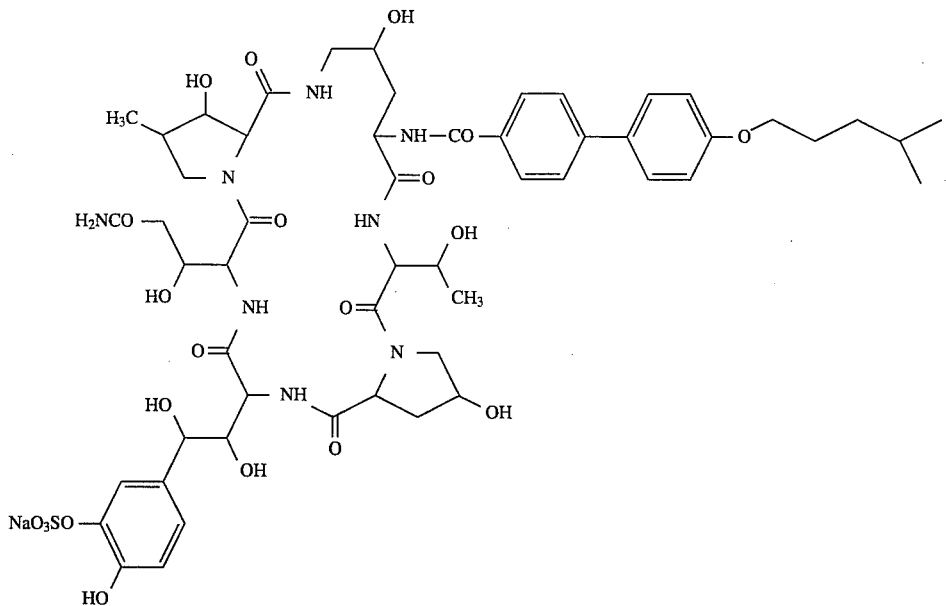 |
| 7 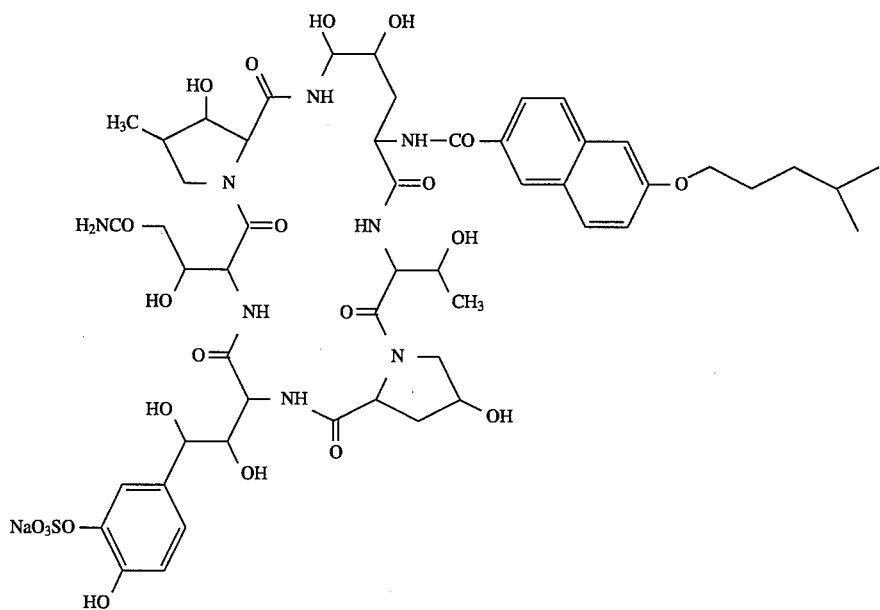 |

| Formula |
|---|
| 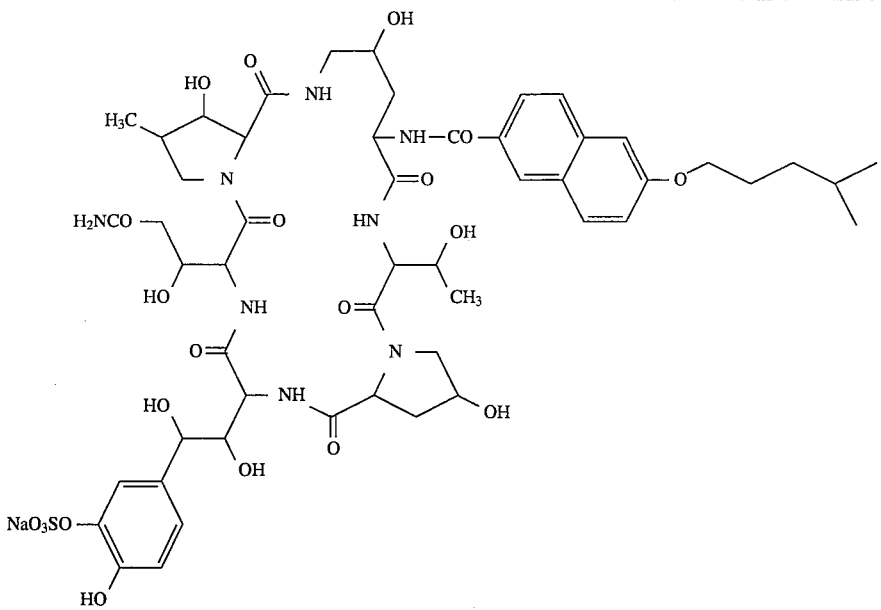 |
| 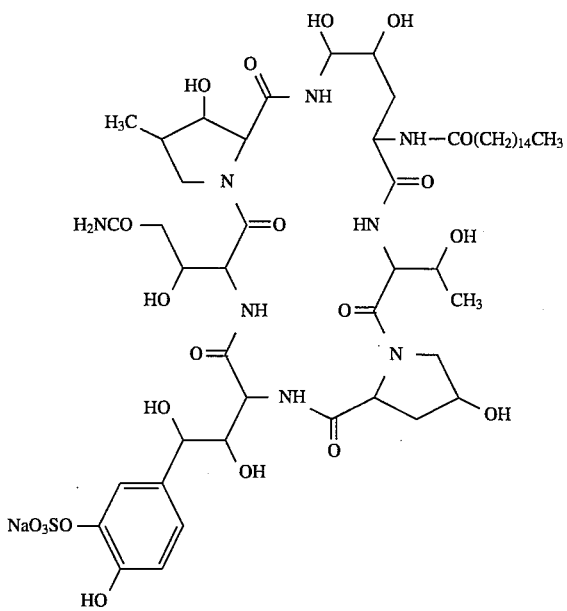 |

| Formula |
|---|
| 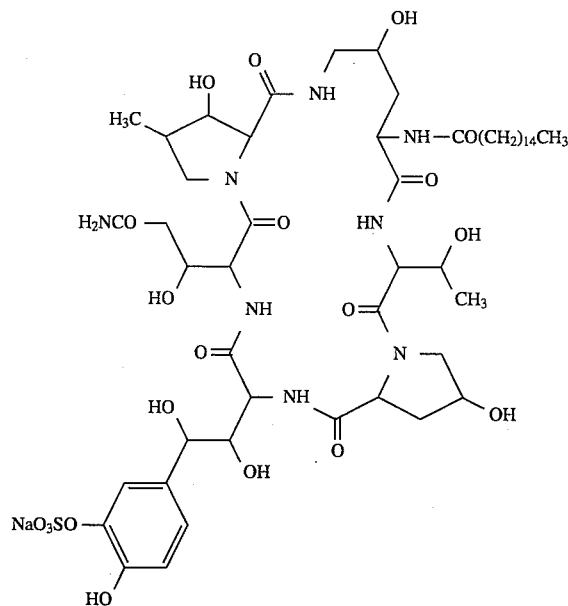 |
| 8 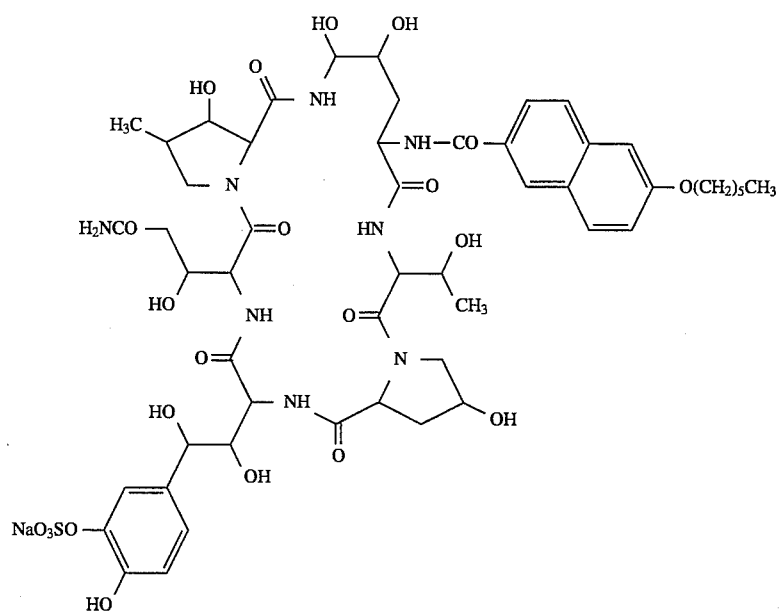 |

| Formula |
|---|
| 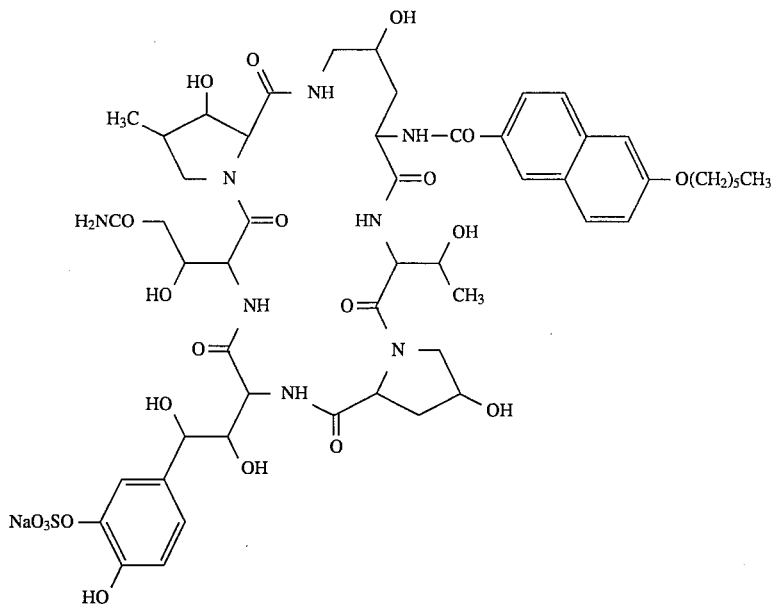 |
| 11 |
| 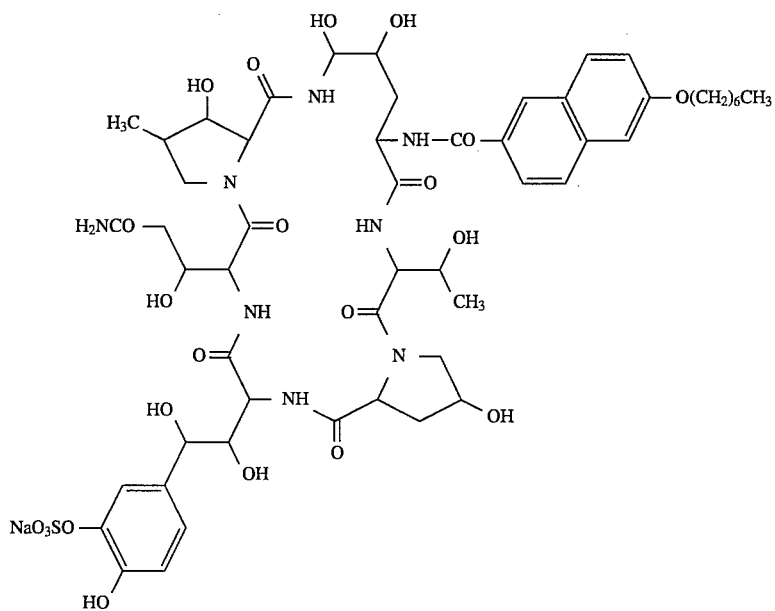 |

-continued
Formula
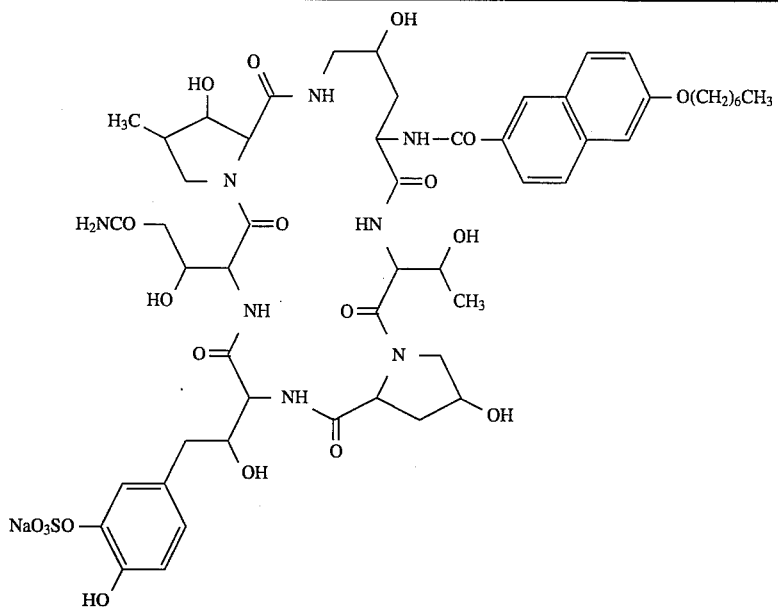
12
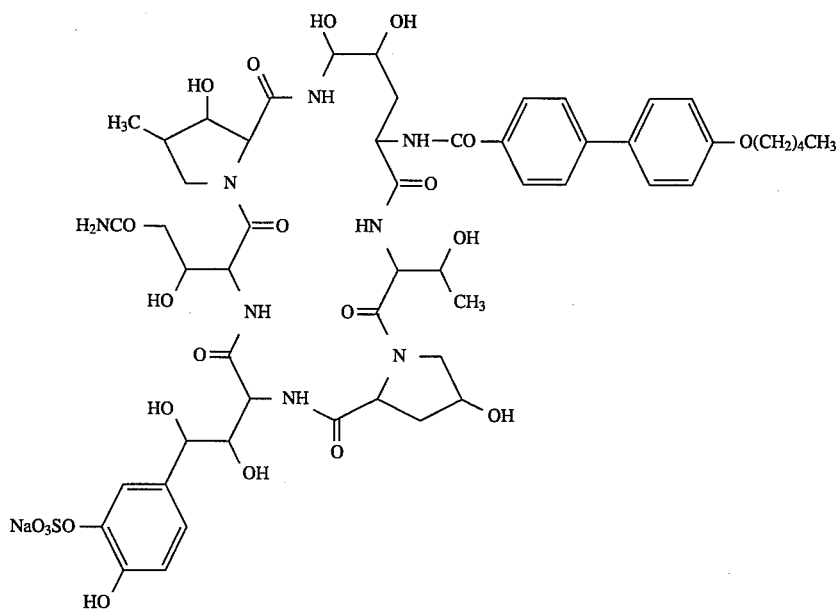

| Formula |
|---|
| 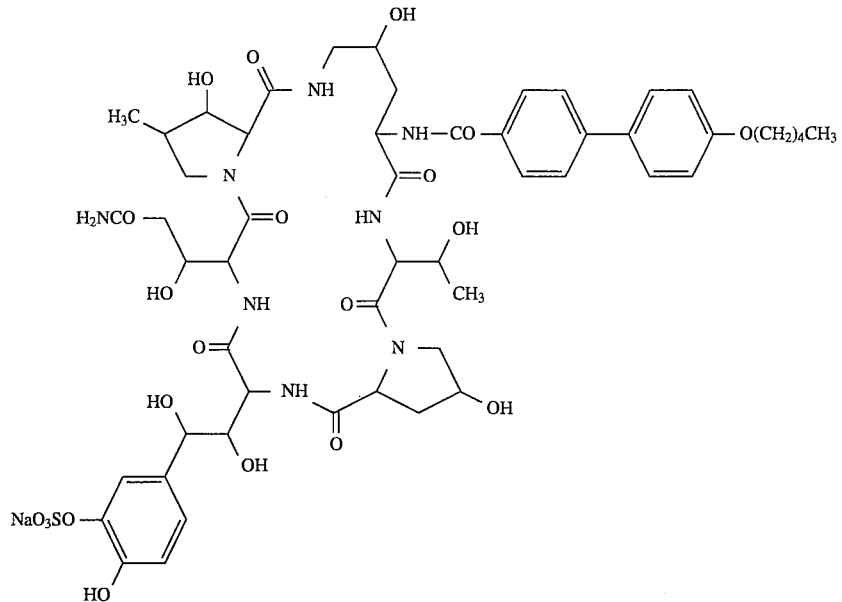 |
| 13 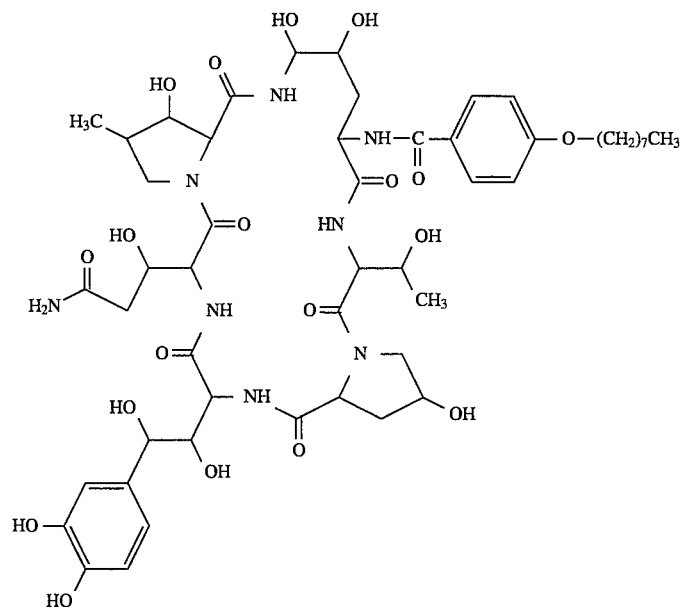 |

5,569,646
| Formula |
|---|
| 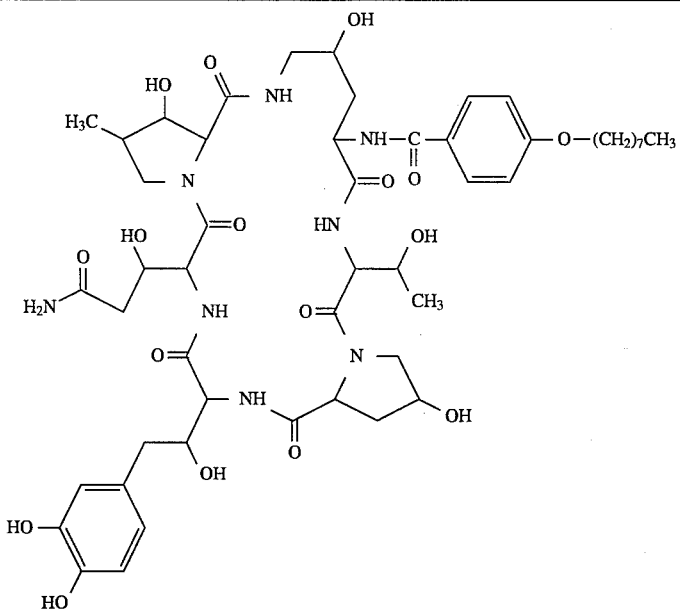 |
| 9 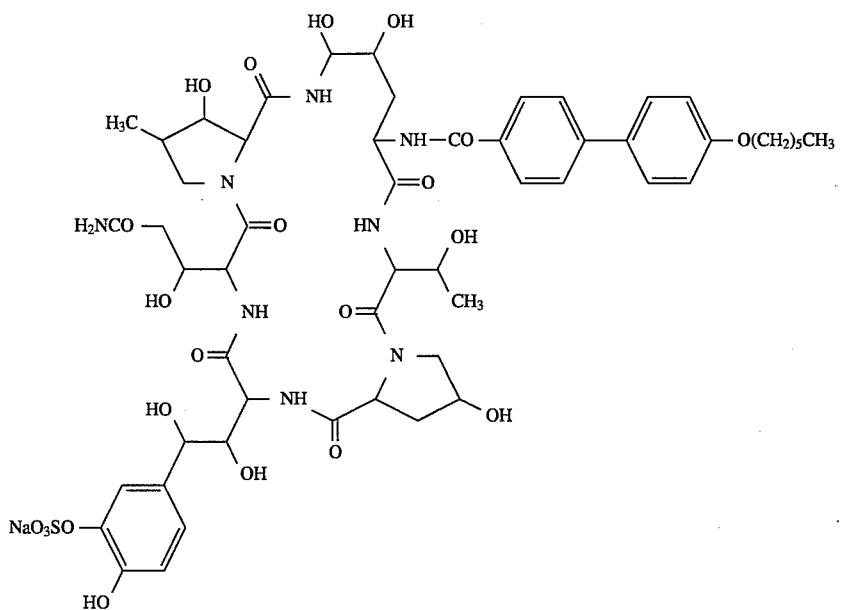 |

| Formula |
|---|
| 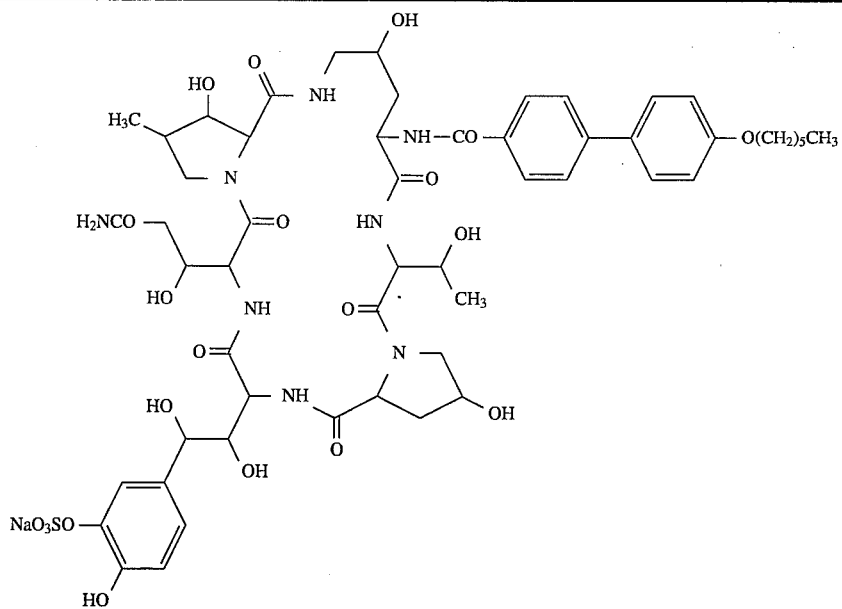 |
| 14 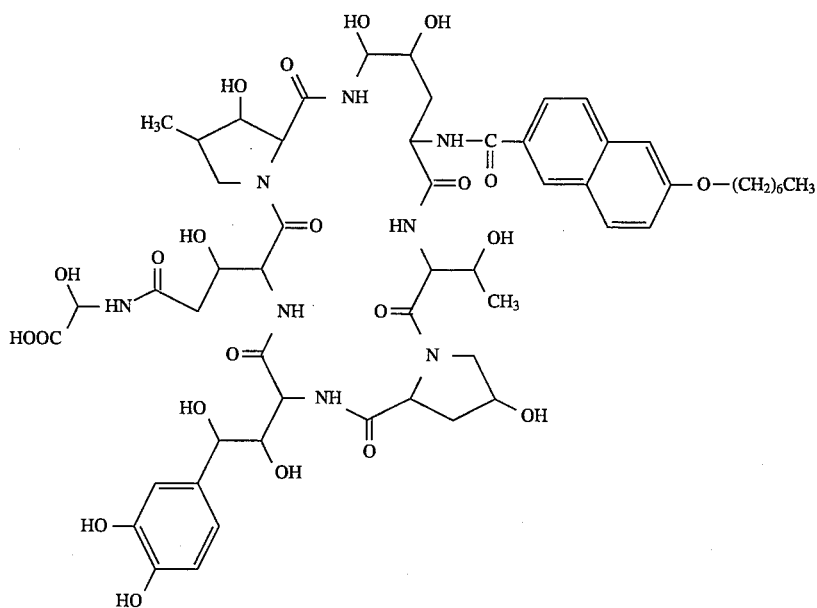 |

| Formula |
|---|
| 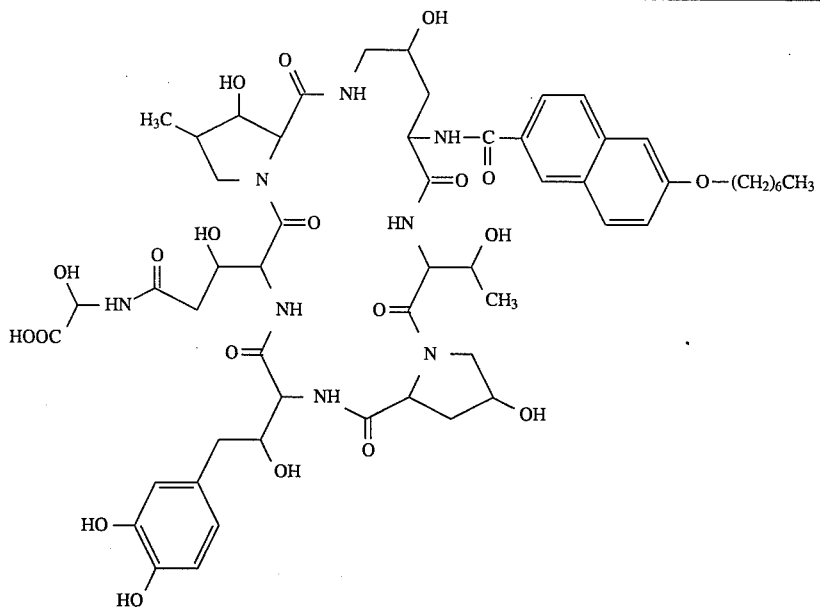 |
| 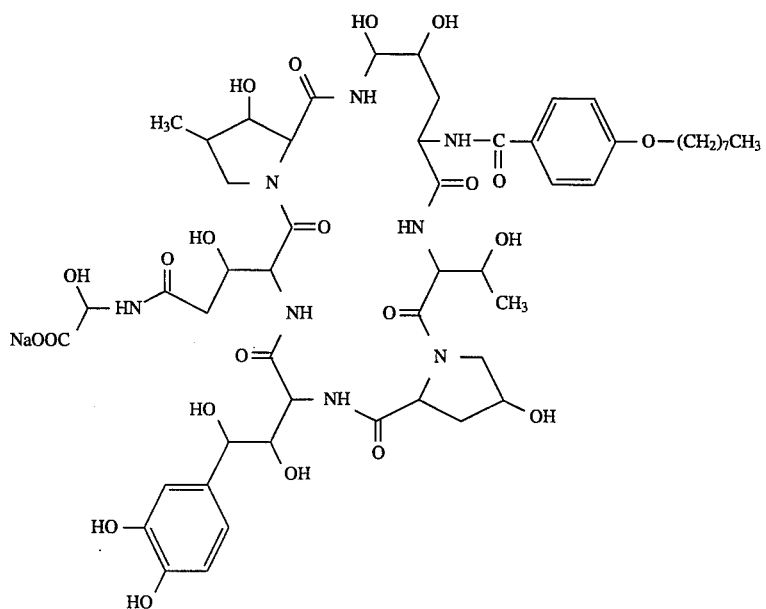 |

| Formula |
|---|
| 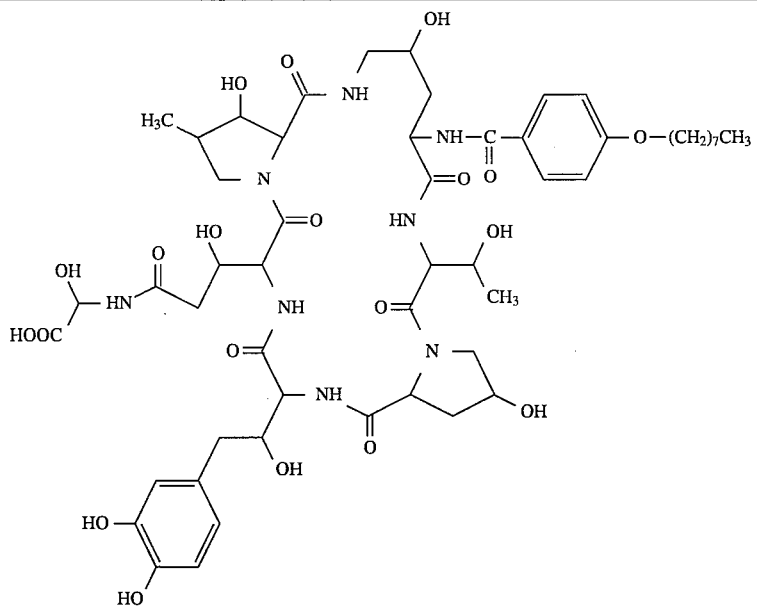 |
| 16 |
| 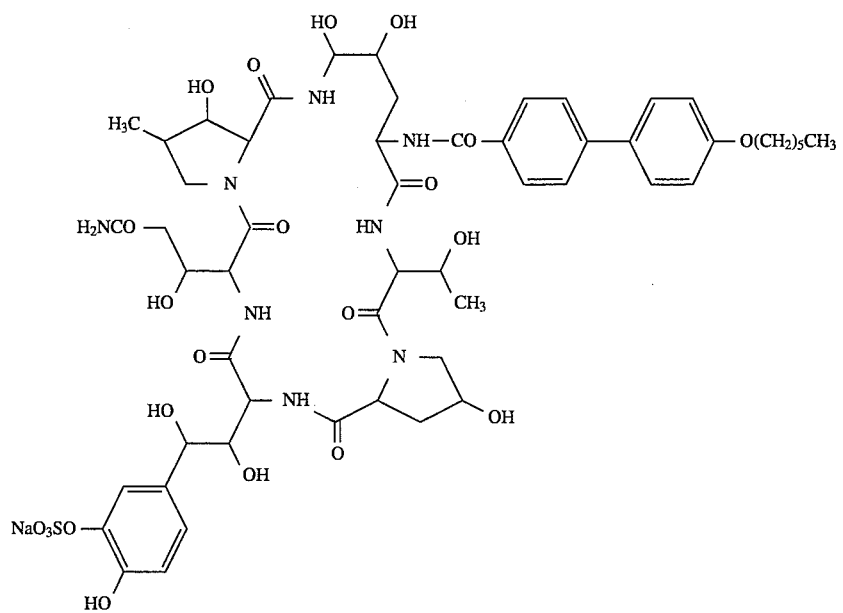 |

-continued
Formula
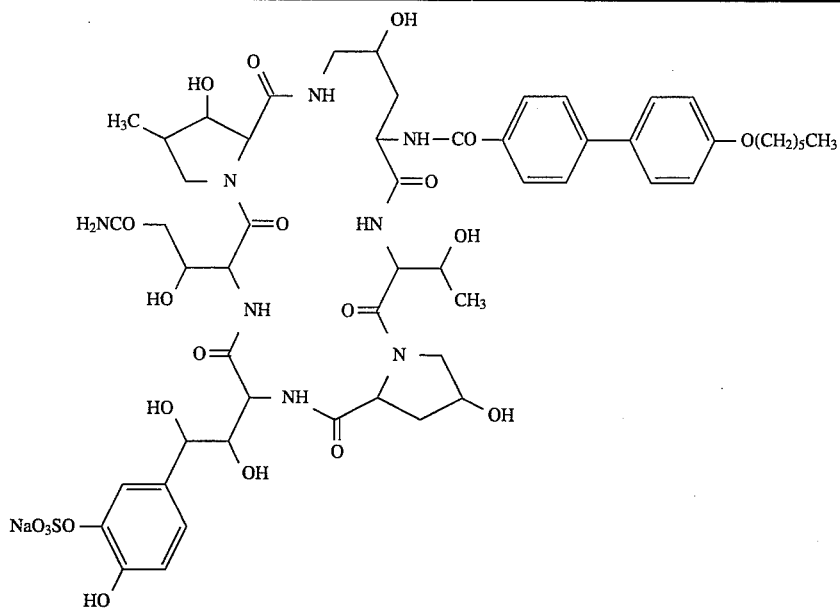
17
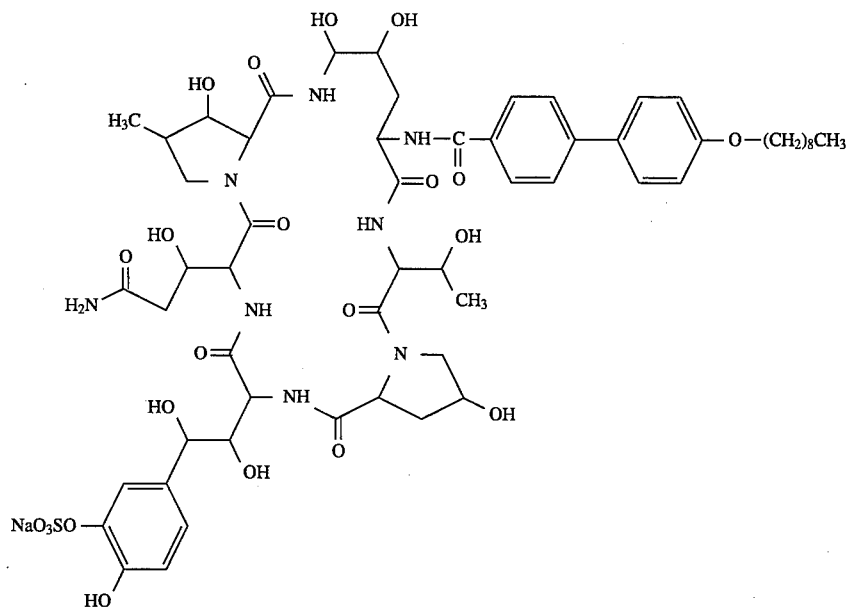

| Formula |
|---|
| 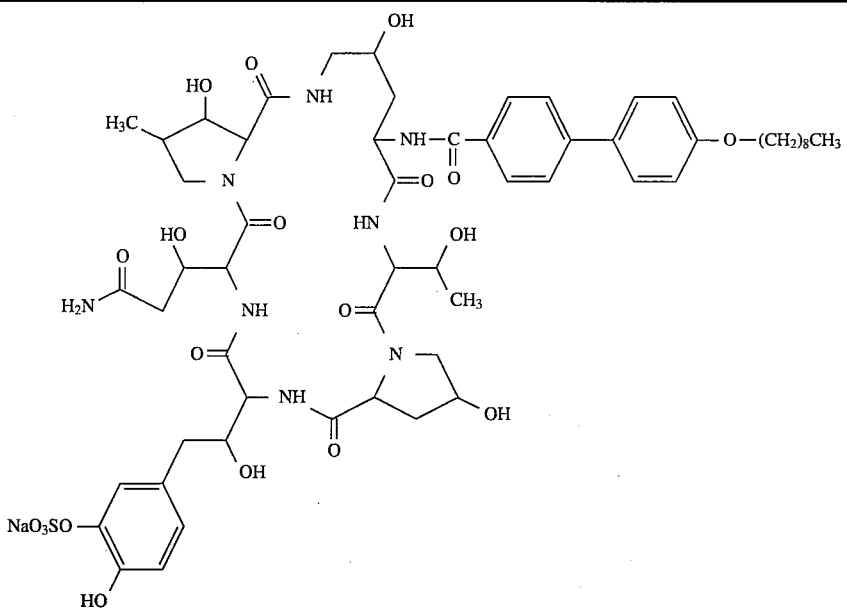 |
| 18 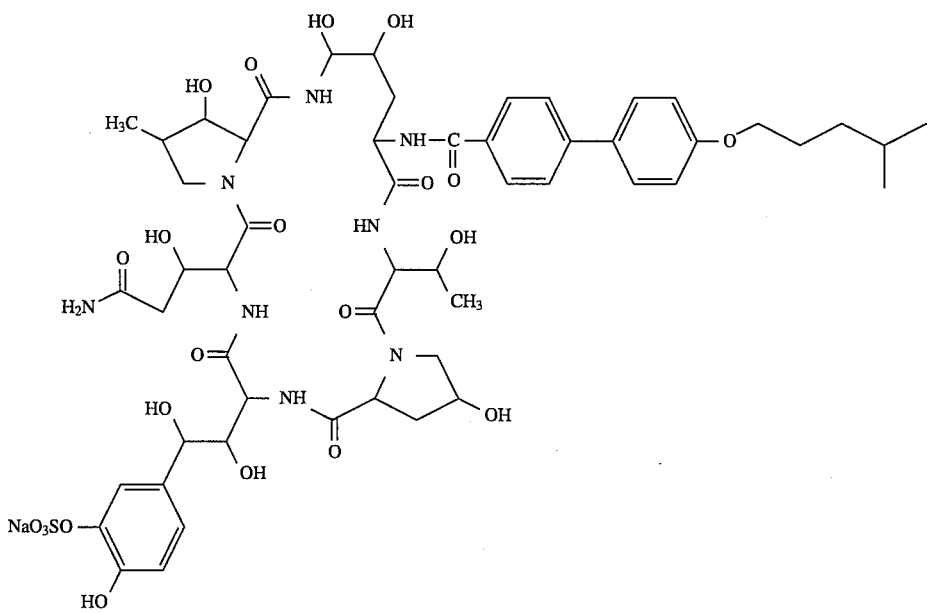 |

| | Formula |
|---|---|
| | 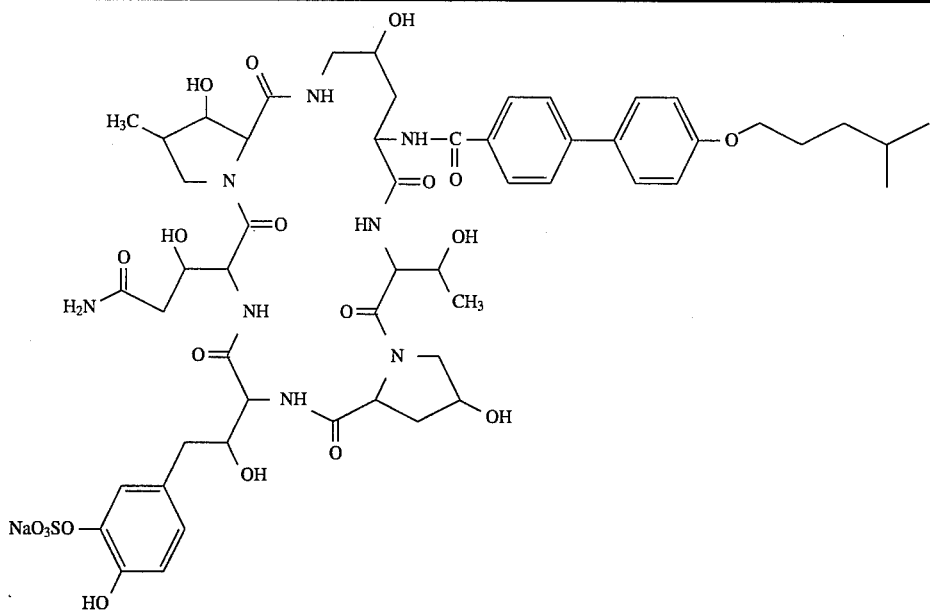 |
| 19 | 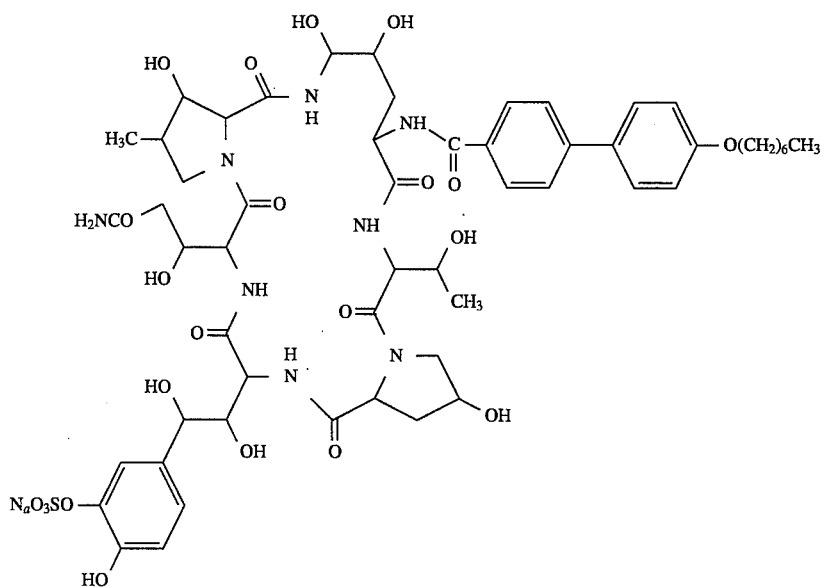 |

| Formula |
|---|
| 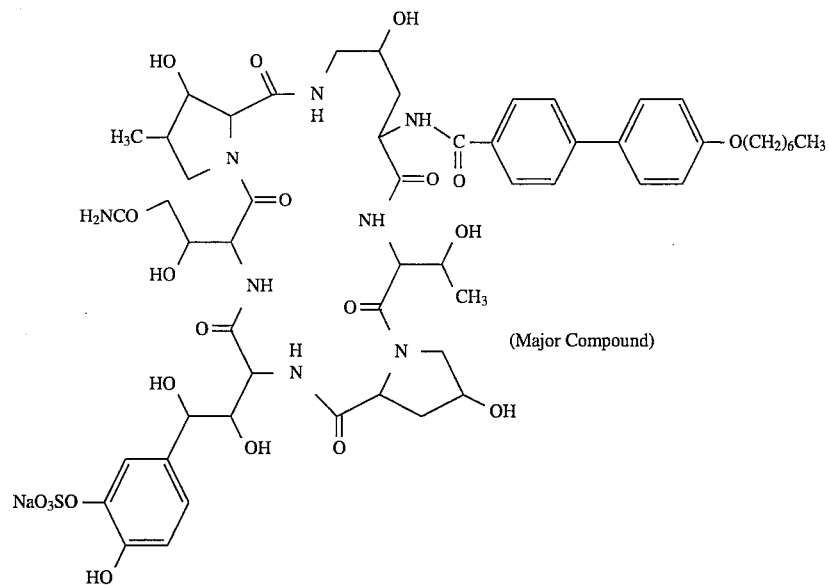
(Major Compound) |
| 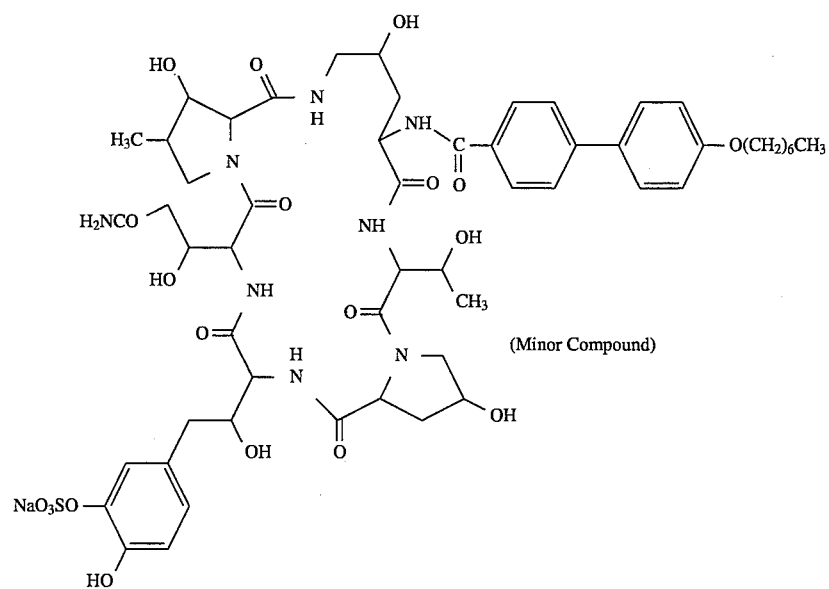
(Minor Compound) |

-continued
Formula
20
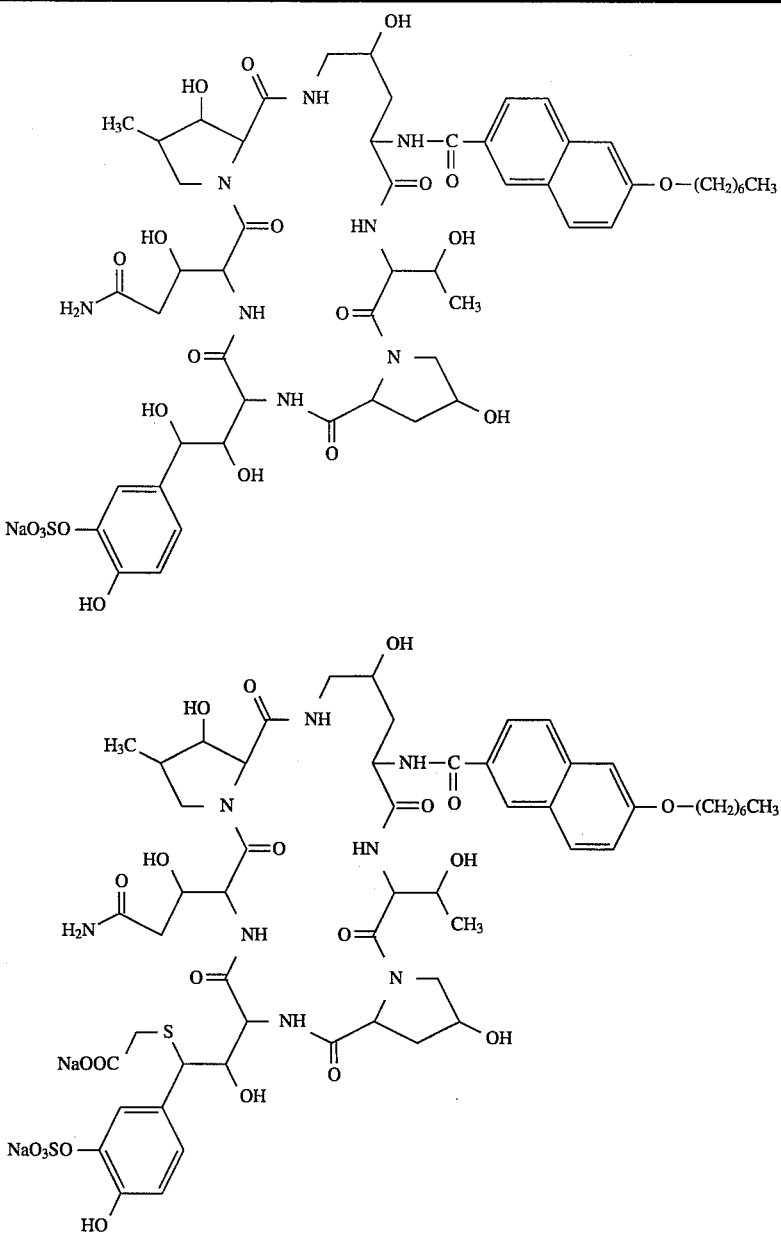

| Formula | |
|---|---|
| 21 | 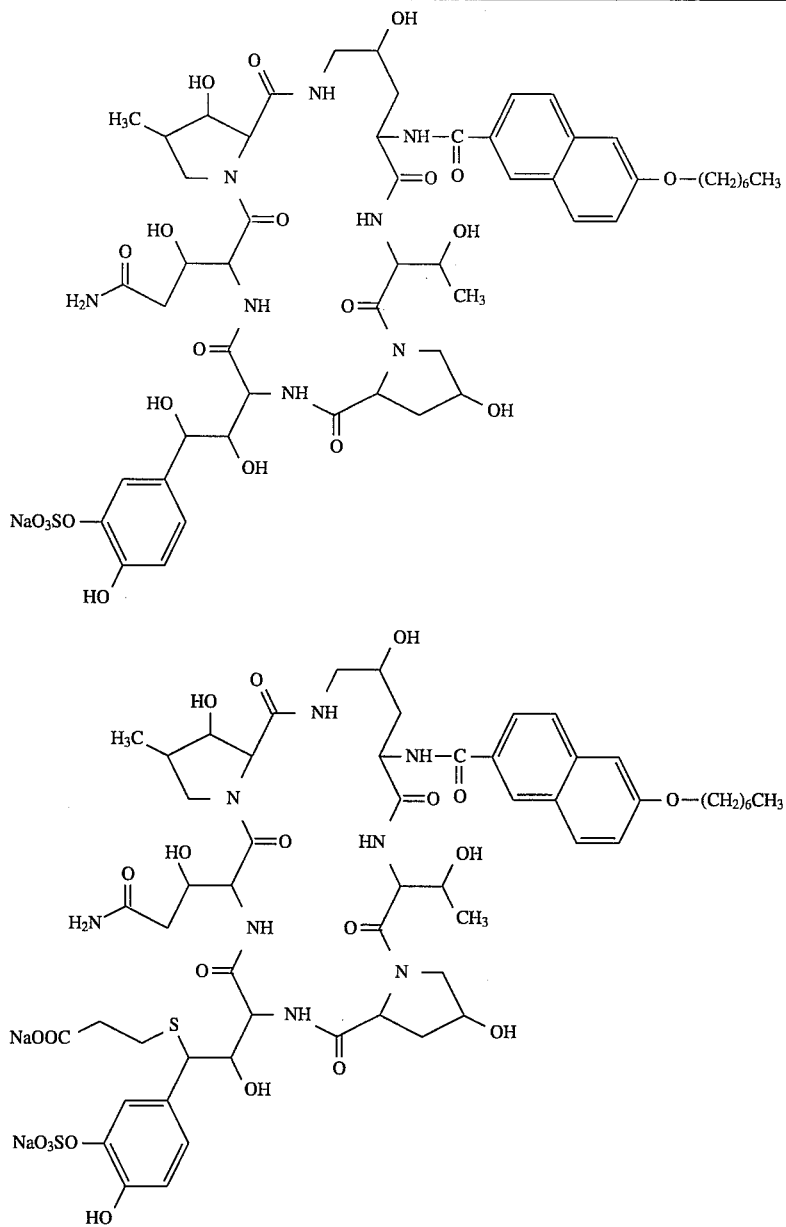 |

-continued

Formula

22

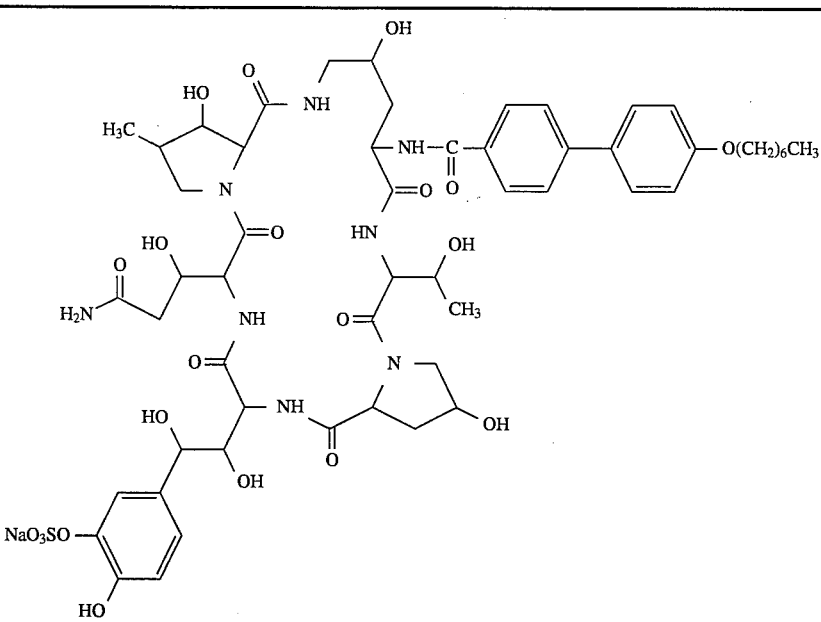

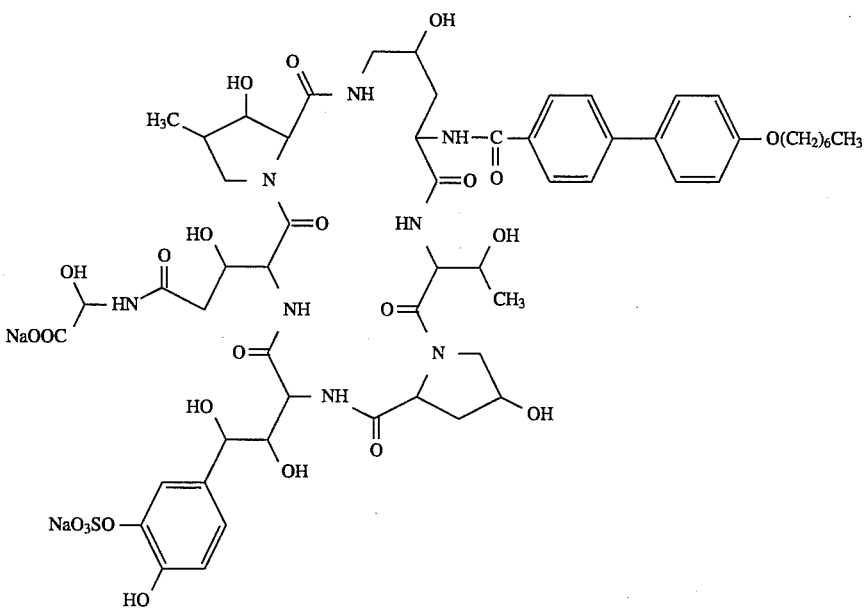

Preparation 10

To a solution of Starting Compound (2.8 g) and succinimido 6-heptyloxy-2-naphthoate (1.46 g) in N,N-dimethylformamide (28 ml) was added 4-(N,N-dimethylamino)pyridine (0.393 g) and stirred for 12 hours at room temparature. The reaction mixture was pulverized with ethyl acetate (140 ml). The precipitate was collected by filtration and dried under reduced pressure. The resultant powder was added to water (50 ml) and subjected to ion-exchange column chromatography on DOWEX-50WX4 (Trademark: prepared by Dow Chemical) (30 ml) and eluted with water. The fractions containing the Object Compound were combined and subjected to column chromatography on ODS YMC-gel (ODS-AM S-50)(Trademark: prepared by Yamamura Chemical Labs) and eluted with 50% aqueous methanol. The fractions containing the Object Compound were combined and evaporated under reduced pressure to remove methanol. The residue was lyophilized to give Object Compound (1.94 g).

IR (Nujol): 3300, 1620 $cm^{-1}$

NMR ($CD_3OD$, $\delta$): 0.92 (3H, t, J=6.6 Hz), 1.06 (3H, d, J=6.8 Hz), 1.24 (3H, d, J=6.1 Hz), 1.3–1.7 (8H, m), 1.7–2.3 (5H, m), 2.3–2.7 (3H, m), 2.8–2.9 (1H, m), 3.39 (1H, m), 3.7–4.7 (16H, m), 4.99 (1H, d, J=2 Hz), 5.10 (1H, d, J=3.7 Hz), 5.36 (1d, J=2.9 Hz), 6.86 (1H, d, J=8.3 Hz), 7.05 (1H, dd, J=8.3 Hz and 2 Hz), 7.17 (1H, dd, J=8.9 Hz and 1.9 Hz), 7.23 (1H, d, J=2 Hz), 7.32 (1H, d, J=1.9 Hz), 7.7–7.9 (3H, m), 8.81 (1H, s)

FAB-MS: e/z=1249 ($M^+$+Na)

Preparation 11

The Object Compound was obtained according to a similar manner to that of Preparation 10

NMR (DMSO-$d_6$, $\delta$): 0.91 (3H, t, J=6.6 Hz), 0.96(3H, d, J=7.2 Hz), 1.09 (3H,d,J=5.5 Hz), 1.25–1.5(4H, m), 1.6–2.6(9H, m), 3.18(1H, m), 3.6–4.6(15H, m), 4.7–5.4 (11H, m), 5.52(1H, d, J=5.8 Hz), 6.74 (1H, d, J=8.2 Hz), 6.83(1H, d, J=8.2 Hz), 6.86(1H, s), 7.04(2H, d, J=8.7 Hz), 7.06(1H, s), 7.2–7.5 (3H, m), 7.68(2H, d, J=8.7 Hz), 7.72 (2H, d, J=8.4 Hz), 7.96(2H, d, J=8.4 Hz), 8.12(1H, d, J=7.9 Hz), 8.31 (1H, d, J=7.1 Hz), 8.77(1H, d, J=7.1 Hz), 8.84(1H, s)

FAB-MS: e/z=1247(M$^+$+Na)

Analysis: Calcd for $C_{53}H_{69}N_8NaO_{22}S\cdot 6H_2O$ C; 47.74 H; 6.12 N; 8.40 Found C; 47.98 H; 5.92 N; 8.41

Preparation 12

The Object Compound was obtained according to a similar manner to that of Preparation 10

NMR (DMSO-$d_6$, δ): 0.85(3H, t, J=6.6 Hz), 0.97 (3H, d, J=6.6 Hz), 1.08(3H, d, J=5.5 Hz), 1.2–1.55(12H, m), 1.65–2.1 (5H, m), 2.1–2.8(4H, m), 3.18(1H, m), 3.65–4.60(15H, m), 4.7–5.2(10H, m), 5.26(1H, d, J=4.4 Hz), 5.53(1H, d, J=5.8 Hz), 6.74 (1H, d, J=8.2 Hz), 6.83(1H, d, J=8.2 Hz), 6.86(1H, s), 7.04(2H, d, J=8.7 Hz), 7.06(1H, s), 7.23–7.55(3H, m), 7.68(2H, d, J=8.7 Hz), 7.72(2H, d, J=8.4 Hz), 7.96 (2H, d, J=8.4 Hz), 8.12(1H, d, J=7.9 Hz), 8.31 (1H, d, J=7.1 Hz), 8.77(1H, d, J=7.1 Hz), 8.85(1H, s)

FAB-MS: e/z=1304(M$^+$+Na)

Analysis: Calcd for $C_{57}H_{77}N_8NaO_{22}S\cdot 5H_2O$ C; 49.92 H; 6.39 N; 8.17 Found C; 49.96 H; 6.44 N; 8.23

Preparation 13

The Object Compound was obtained according to a similar manner to that of Preparation 10

IR(KBr): 3300, 1668, 1628, 1271, 1216 cm$^{-1}$

NMR (DMSO-$d_6$, δ): 0.91 (6H, d, J=6.6 Hz), 0.96 (3H, d, J=6.7 Hz), 1.08(3H, d, J=5.5 Hz), 1.25–1.45(2H, m), 1.5–2.7(10H, m), 3.18(1H, m), 3.72(2H, m), 3.85–4.6 (13H, m), 4.73–5.23(10H, m), 5.26(1H, d, J=4.5 Hz), 5.52(1H, d, J=5.9 Hz), 6.74 (1H, d, J=8.1 Hz), 6.83(1H, d, J=8.1 Hz), 6.91 (1H, s), 7.05(1H, s), 7.19–7.52(5H, m), 7.84(1H, d, J=8.7 Hz), 7.9–8.0(2H, m), 8.13(1H, d, J=7.9 Hz), 8.33(1H, d, J=7.1 Hz), 8.44(1H, s), 8.80(1H, d, J=7.1 Hz), 8.85(1H, s)

FAB-MS: e/z=1235(M$^+$+Na)

Analysis: Calcd for $C_{52}H_{69}N_8NaO_{21}S\cdot 4H_2O$ C; 48.59 H; 6.04 N; 8.72 Found C; 48.53 H; 6.15 N; 8.54

Preparation 14

To a solution of Starting Compound (0.2 g) in the mixture of N,N-dimethylformamide (2 ml) and acetone (2 ml) in presence of molecular sieves 4A was added glyoxylic acid (0.155 g) at room temperature. The mixture was stirred at the same temperature for 5 hours. The reaction mixture was pulverized with ethyl acetate (20 ml). The precipitate was collected by filtration and dried under reduced pressure to give Object Compound (0.14 g).

NMR (CD$_3$OD, δ): 0.90 (3H, t, J=6.6 Hz), 1.05 (3H, d, J=6.7 Hz), 1.24 (3H, d, J=6.0 Hz), 1.2–1.6 (10H, m), 1.7–1.9 (2H, m), 1.9–2.2 (3H, m), 2.3–2.6 (3H, m), 2.7–2.9 (1H, m), 3.40 (1H, m), 3.7–4.7 (16H, m), 4.98 (1H, s), 5.09 (1H, brs), 5.31 (1H, brs), 5.40 (1H, s), 6.8–7.2 (4H, m), 7.33 (1H, s), 7.85 (2H, d, J=8.4 Hz).

FAB-MS: e/z=1287 (M$^+$+Na)

Preparation 15

The Object Compound was obtained according to a similar manner to that of Preparation 14.

IR (Nujol): 3250, 1610 cm$^{-1}$

NMR (CD$_3$OD, δ): 0.90 (3H, t, J=6, 6 Hz), 1.05 (3H, d, J=6.7 Hz), 1.24 (3H, d, J=6.1 Hz), 1.2–1.6 (10H, m), 1.7–1.9 (2H, m), 1.9–2.2 (3H,m), 2.3–2.6 (3H, m), 2.7–2.9 (1H, m), 3.42 (1H, m), 3.7–4.7 (16H, m), 4.98 (1H, s), 5.09 (1H, d, J=3.8 Hz), 5.31 (1H, d, J=2.8 Hz), 5.44 (1H, s), 6.60 (1H, dd, J=8.1 and 1.9 Hz), 6.72 (1H, d J=8.1 Hz), 6.82 (1H, d, J=1.9 Hz), 6.95 (2H, d, J=8.8 Hz) 7.84 (2H, d, J=8.8 Hz).

FAB-MS: e/z=1185 (M$^+$+Na)

Elemental Analysis: Calcd: for $C_{52}H_{73}N_8NaO_{22}\cdot 7H_2O$ C; 47.63 H; 6.76 N; 8.54 Found: C; 47,56 H; 6.66 N; 8.35

Preparation 16

The Object Compound was obtained accordina to a similar manner to that of Preparation 14.

NMR (DMSO-$d_6$, δ): 0.88 (3H, t, J=6.6 Hz), 0.96 (3H, d, J=6.7 Hz), 1.12 (3H, d, J=5.9 Hz), 1.2–2.0 (13H, m), 2.1–2.7 (4H, m), 3.15 (1H, m), 3.5–4.5 (18H, m), 4.7–5.7 (1H, m), 6.74 (1H, d, J=8.2 Hz), 6.84 (1H, d, J=8.5 Hz), 7.03 (1H, s), 7.22 (1H, d, J=8.9 Hz), 7.36 (1H, s), 7.5 (1H, m), 7.83 (1H, d, J=8.8 Hz), 7.9–8.0 (2H, m), 8.0–8.3 (3H, m), 8.49 (1H, s), 8.65 (1H, m), 8.85 (1H, brs)

FAB-MS: e/z=1324 (M$^+$)

Elemental Analysis: Calcd: for $C_{55}H_{72}N_8Na_2O_{25}S\cdot 7H_2O$ C; 45.57 H; 5.98 N; 7.73 Found: C; 45.72 H; 5.87 N; 7.69

Preparation 17

To a solution of Starting Compound (3.15 g) in N,N-dimethylformamide (32 ml) was added the mixture of trifluoroacetic acid (0.37 ml) and p-toluenesulfonic acid·H$_2$O (0.5 g) at room temperature and stirred for 12 hours at the same temperature. The reaction mixture was pulverized with ethyl acetate (300 ml). The precipitate was collected by filtration and dried under reduced pressure to give crude product (3.3 g). The crude product (0.6 g) was added to water (100 ml) and purified by preparative HPLC utilizing a C$_{18}$ μ Bondapak resin (Waters Associates, Inc.) which was eluted with a solvent system comprised of acetonitrile-pH 3 phosphate buffer (38:62) at a flow rate of 80 ml/minutes using a Shimadzu LC-8A pump. The column was monitored by a UV detector set at 240 nm. The fractions containing the major compound at retention time of 20.6 minutes were combined and evaporated under reduced pressure to remove acetonitrile. The residue was adjusted to pH 6.5 with saturated sodium bicarbonate aqueous solution and subjected to column chromatography on ODS (YMS-gel ODS-AM S-50) and washed with water and eluted with 80% methanol aqueous solution. The fractions containing the Object Compound were combined and evaporated under reduced pressure to remove methanol. The residue was lyophilized to give Object Compound (147 mg).

IR (Nujol): 3300, 1620 cm$^{-1}$

NMR (DMSO-$d_6$, δ); 0.88 (3H, t, J=6.6 Hz), 0.94 (2H, t, J=6.7 Hz), 1.09 (3H, d, J=5.9 Hz), 1.2–2.0 (13H, m), 2.1–2.7 (4H, m), 8.20 (1H, m), 3.6–4.5 (18H, m), 4.7–5.2 (10H, m), 5.4–5.6 (2H, m), 6.44 (1H, d,J=8.2 Hz), 6.6 (1H, d, J=8.2 Hz), 6.70 (1H, s), 7.1–7.5 (3H, m), 7.7–8.2 (6H, m), 8.3–8.9 (5H, m)

EXAMPLE 1

To a solution of Starting Compound (1 g) in trifluoroacetic acid (5 ml) in presence of molecular sieves 4 Å was added sodium cyanoborohydride (0.285 g) at ambient temperature. The mixture was stirred for an hour at the same temperature. The reaction mixture was added to water (10 ml) under ice-cooling and adjusted to pH 7 with 1N aqueous sodium hydroxide. The solution was subjected to ion-exchange column chromatography on DOWEX-50WX4 (Na$^+$ Type) (30 ml) and eluted with water. The fractions containing the Object Compound were combined and purified by preparative HPLC utilizing a C18 μ Bondapak resin (Waters Associates Inc.) which was eluted with a solvent system composed of acetonitrile-pH3 phosphate buffer (39:61) at a flow rate of 80 ml/minute using a Shimadzu LC-8A pump. The column was monitored by a UV detector set at 240 nm. The fractions containing the first eluted compound at retention time of 17.1 minute were combined and evaporated under reduced pressure to remove acetonitrile. The residue was subjected to column chromatography on ODS (YMC-gel ODS-AMS-50) and washed with water and eluted with 80% aqueous methanol. The fractions containing the Object Compound were combined and evaporated under reduced pressure to remove methanol. The residue was lyophilized to give Object Compound 1 (318 mg).

IR (Nujol): 3300, 1610, 1230 cm$^{-1}$

NMR (DMSO-d$_6$, δ): 0.86 (3H, t, J=6.6 Hz), 0.95 (3H, d, J=6.7 Hz), 1.09 (3H, d, J=5.9 Hz), 1.2–2.0 (15H, m), 2.1–2.6 (4H, m), 3.00 (1H, m), 3.19 (1H, m), 3.74 (2H, m), 3.8–4.5 (14H, m), 4.6–5.4 (10H, m), 6.73 (1H, d, J=8.2 Hz), 6.80 (1H, s), 6.84 (1H, dd, J=8.2 and 1.9 Hz), 6.97 (2H, d, J=8.8 Hz), 7.06 (1H, d, J=1.9 Hz), 7.25 (1H, s), 7.44 (2H, m), 7.69 (1H, m), 7.83 (2H, d, J=8.8 Hz), 8.09 (1H, d, J=7 Hz), 8.44 (1H, d, J=7 Hz), 8.85 (1H, s)

FAB-MS: e/z=1197 (M$^+$+Na)

Elemental Analysis: Calcd. for C$_{50}$H$_{71}$N$_8$NaO$_{21}$S•6H$_2$O C; 46.79 H; 6.51 N; 8.73 Found: C; 46.84 H; 6.27 N; 8.73

The second eluted compound at retention time of 20.2 min. was obtained according to a similar manner to that of the first eluted compound, Object Compound 2 (263 mg).

IR (Nujol): 3250, 1600, 1490, 1240 cm$^{-1}$

NMR (DMSO-d$_6$, δ); 0.86 (3H, t, J=6.6 Hz), 0.95 (3H, d, J=6.7 Hz), 1.09 (3H, d, J=5.9 Hz), 1.2–2.0 (15H, m), 2.1–2.6 (6H, m), 2.96 (1H, m), 3.21 (1H, m), 3.6–4.5 (16H, m,), 4.6–5.4 (8H, m), 6.73 (1H, d, J=8.2 Hz), 6.77 (1H, dd, J=8.2 and 1.9 Hz), 6.81 (1H, s), 6.97 (2H, d, J=8.8 Hz), 6.98 (1H, d, J=1.9 Hz), 7.25 (1H, s), 7.39 (2H, m), 7.39 (1H, m), 7.74 (1H, m), 7.84 (2H, d, J=8.8 Hz), 8.14 (1H, d, J=7 Hz), 8.46 (1H, m), 8.72 (1H, s)

FAB-MS: e/z=1181 (M$^+$+Na)

Elemental Analysis: Calcd. for C$_{50}$H$_{71}$N$_8$NaO$_{20}$S•6H$_2$O C; 47.38 H; 6.60 N; 8.84 Found: C; 47.46 H; 6.62 N; 8.83

EXAMPLE 2

To suspension of Starting Compound (10.4 g) and sodium cyanoborohydride (1.67 g) in dichloromethane (52 ml) was gradually added tetrahydrofuran (104 ml) at 5° C. The mixture was stirred at 40° C. for 1 hour. The reaction mixture was evaporated under reduced pressure. To the residue was added water, adjust to pH8.5 with 1N sodium hydroxide and subjected to column chromatography on ODS(YMC-gel, ODS-AM S-50) and eluted with 60% acetonitrile aq. The fractions containing the crude product were combined and evaporated under reduced pressure to remove acetonitrile. The residue was lyophilized to give crude powder (10.1 g). The crude powder was purified by column chromatography on silica gel using dichloromethane/acetic acid/methanol/water(4:1:1:1) as eluent. The fractions containing the Object Compound were combined and evaporated under reduced pressure. To the residue was added water, adjusted to pH8.5 with 1N sodium hydroxide and subjected to column chromatography on ODS (YMC-gel ODS-AM S-50) and eluted with 60% acetonitrile aq. The fractions containing the Object Compound were combined and evaporated under reduced pressure to remove acetonitrile. The residue was lyophilized to give Object Compound (2.25 g).

IR(Nujol): 3250, 1600, 1490, 1240 cm$^{-1}$

NMR (DMSO-d$_6$, δ): 0.86(3H, t, J=6.6 Hz), 0.95 (3H, d, J=6.7 Hz), 1.09(3H, d, J=5.9 Hz), 1.2–2.0(15H, m), 2.1–2.6 (6H, m), 2.96(1H, m), 3.21 (1H, m 3.6–4.5(16H, m,), 4.6–5.4(8H, m), 6.73 (1H, d, J=8.2 Hz), 6.77(1H, dd, J=8.2 and 1.9 Hz), 6.81 (1H, s), 6.97 (2H, d, J=8.8 Hz), 8.14 (1H, d, J=7 Hz), 8.46 (1H, m), 8.72 (1H, s)

FAB-MS: e/z=1181 (M$^+$+Na)

Elemental Analysis: Calcd. for C$_{50}$H$_{71}$N$_8$NaO$_{20}$S•6H$_2$O C; 47.38 H; 6.60 N; 8.84 Found: C; 47.46 H; 6.62 N; 8.83

EXAMPLE 3

To a suspension of Starting Compound (1g) and sodium cyanoborohydride (0.256 g) in dichloromethane (10 ml) was gradually added tetrahydrofuran (5 ml) at 5° C. The mixture was stirred at 5° C. for 1.5 hours. The reaction mixture was pulverized with diisopropyl ether (200 ml). The precipitate was collected by filtration and dried under reduced pressure. The powder was purified by column chromatography on silica gel using dichloromethane/acetic acid/methanol/water(3:1:1:1) as eluent. The fractions containing the Object Compound were combined and evaporated under reduced pressure. To the residue was added water, adjusted to pH 8.5 with 1N sodium hydroxide and subjected to column chromatography on ODS (YMC-gel ODS-AM S-50) and eluted with 60% acetonitrile aq. The fractions containing the Object Compound were combined and evaporated under reduced pressure to remove acetonitrile. The residue was lyophilized to give Object Compound (0.21 g).

IR (Nujol): 3300, 1620, 1270 cm$^{-1}$

NMR (DMSO-d$_6$, δ): 0.88(3H, t, J=6.6 Hz), 0.96 (3H, d, J=6.8 Hz), 1.12(3H, d, J=5.9 Hz), 1.2–1.55(8H, m), 1.65–2.6(9H, m), 2.97 (1H, m), 3.20(1H, m), 3.26–3.52 (1H, m), 3.73(2H, m), 3.86–4.63(14H, m), 4.63–5.36(9H, m), 6.74(1H, d, J=8 Hz), 6.83(1H, dd, J=1.5 and 8 Hz), 6.92(1H, s), 7.06(1H, d, J=1.5 Hz), 7.2–7.35(2H, m), 7.35–7.6(3H, m), 7.68(1H, m), 7.8–8.0(3H, m), 8.09(1H, d, J=8 Hz), 8.42(1H, s), 8.67(1H, d, J=6.9 Hz), 8.71 (1H, s)

FAB-MS: e/z=1233(M$^+$+Na)

Elemental Analysis: Calcd: for C$_{53}$H$_{71}$N$_8$NaO$_{21}$S•6H$_2$O C; 48.25 H; 6.34 N; 8.49 Found: C; 48.06 H; 6.29 N; 8.31

EXAMPLE 4

The Object Compound was obtained according to a similar manner to that of Example 3.

NMR (DMSO-d$_6$, δ): 0.9–1.1 (6H, m), 1.11 (3H, d, J=5.8 Hz), 1.3–1.5(4H, m), 1.7–2.1 (5H, m), 2.2–2.4(4H, m), 2.9–3.1(2H, m), 3.4 (1H, m), 3.7–4.5(16H, m), 4.7–5.3 (9H, m), 6.7–7.1(6H, m), 7.22(1H, s), 7.41 (1H, d, J=8.5 Hz), 7.6–7.8(5H, m), 7.93(2H, d, J=8.2 Hz), 8.08(1H, d, J=8.5 Hz), 8.60(1H, d, J=7.1 Hz), 8.85(1H, s)

FAB-MS: e/z=1231(M$^+$+Na)

Elemental Analysis: Calcd for C$_{53}$H$_{69}$N$_8$NaO$_{21}$S•3.5H$_2$O C; 50.04 H; 6.02 N; 8.87 Found C; 50.05 H; 6.25 N; 8.81

EXAMPLE 5

The Object Compound was obtained according to a similar manner to that of Example 3.

IR(Nujol): 3300, 1635, 1247, 1047 cm$^{-1}$ NMR (DMSO-d$_6$, δ): 0.86(3H, t, J=6.7 Hz), 0.95(3H, d, J=6.7 Hz), 1.10(3H, d, J=5.8 Hz), 1.2–1.6(12H, m), 1.6–2.6(9H, m), 3.0(1H, m), 3.2(1H, m), 3.4(1H, m), 3.74(2H, m), 3.83–4.6(14H, m), 4.65–5.4 (9H, m), 6.73(1H, d, J=8.2 Hz), 6.81(1H, dd, J=1.7 and 8.2 Hz), 6.89(1H, s), 7.03 (2H, d, J=8.8 Hz), 7.05(1H, d, J=1.7 Hz), 7.23(1H, s), 7.41 (2H, m), 7.6–7.8(1H, m), 7.67(2H, d, J=8.8 Hz), 7.71(2H, d, J=8.5 Hz), 7.93(2H, d, J=8.5 Hz), 8.05(1H, d, J=8 Hz), 8.62(1H, d, J=6.7 Hz), 8.84 (1H, s)

FAB-MS: e/z=1287(M$^+$+Na)

83

Elemental Analysis: Calcd for $C_{57}H_{77}N_8NaO_{21}S \cdot 8H_2O$
C; 48.57 H; 6.65 N; 7.95 Found C; 48.41 H; 6.26 N; 7.89

EXAMPLE 6

The Object Compound was obtained according to a similar manner to that of Example 3.

IR(Nujol): 3300, 1633, 1247, 1047 $cm^{-1}$

NMR (DMSO-$d_6$,δ): 0.90(6H, d, J=6.5 Hz), 0.95(3H, d, J=6.8 Hz), 1.10(3H, d, J=5.7 Hz), 1.31 (2H, q, J=7.5 Hz), 1.45–2.6 (12H, m), 2.97(1H, m), 3.18(1H, m), 3.40 (1H, m), 3.74(2H, m), 3.83–5.4(23H, m), 6.72(1H, d, J=8.2 Hz), 6.81 (1H, d, J=8.2 Hz), 6.89(1H, s), 7.03(2H, d, J=8.9 Hz), 7.06(1H, s), 7.2–7.6(3H, m), 7.6–7.8 (1H, m), 7.67(2H, d, J=8.9 Hz), 7.71 (2H, d, J=8.4 Hz), 7.93(2H, d, J=8.4 Hz), 8.05 (1H, m), 8.61(1H, d, J=6.7 Hz), 8.84(1H, s)

FAB-MS: e/z=1245($M^+$+Na)

Elemental Analysis: Calcd for $C_{54}H_{71}N_8NaO_{20}S \cdot 7H_2O$
C; 48.64 H; 6.43 N;8.40 Found C; 48.72 H; 6.25 N; 8.26

EXAMPLE 7

The Object Compound was obtained according to a similar manner to that of Example 3.

IR(Nujol): 3300, 1625 $cm^{-1}$

NMR (DMSO-$d_6$, δ): 0.91(6H, d, J=6.6 Hz), 0.95(3H, d, J=6.7 Hz), 1.10(3H, d, J= 5.4 Hz), 1.28–1.47(2H, m), 1.5–2.6 (10H, m), 2.97(1H, m), 3.18(1H, m), 1H, m), 3.40(1H, m), 3.74(2H, m), 3.87–5.45(23H, m), 6.71 (1H, d, J=8.3 Hz), 6.79(1H, d, J=8.3 Hz), 6.91(1H, s), 7.05(1H, s), 7.18–7.58(5H, m), 7.69(1H, m), 7.8–8.0(3H, m), 8.42 (1H, s), 8.60(1H, d, J=6.7 Hz)

FAB-MS: e/z=1219($M^+$+Na)

Elemental Analysis: Calcd for $C_{52}H_{69}N_8NaO_{21}S \cdot 7H_2O$
C; 47.20 H;6.32 N;8.47 Found C; 47.43 H; 6.37 N; 8.34

EXAMPLE 8

The Object Compound was obtained according to a similar manner to that of Example 3.

IR(Nujol): 3300, 1620, 1272 $cm^{-1}$

NMR (DMSO-$d_6$, δ): 0.89(3H, t, J=6.7 Hz), 0.95(3H, d, J=6.9 Hz), 1.11 (3H, d, J=5.8 Hz), 1.25–1.6(6H, m), 1.65–2.6(9H, m), 2.97(1H, m), 3.20(1H, m), 3.40(1H, m), 3.74(2H, m), 3.87–5.53(23H, m), 6.73 (1H, d, J=8.2 Hz), 6.82(1H, dd, J=1.7 and 8.2 Hz), 6.91(1H, s), 7.04(1H, d, J=1.7 Hz), 7.23(1H, dd, J=2, 8.9 Hz), 7.29 (1H, s), 7.37(1H, d, J=2 Hz), 7.47(2H, m), 7.70(1H, m), 7.8–8.0(3H, m), 8.07(1H, d, J=8Hz), 8.42 (1H, s), 8.64(1H, d, J=6.9 Hz), 8.85(1H, s)

FAB-MS: e/z=1219($M^+$+Na)

Analysis: Calcd for $C_{52}H_{69}N_8NaO_{21}S \cdot 6H_2O$ C; 47.85 H; 6.25 N; 8.58 Found C; 48.03 H; 6.01 N; 8.39

EXAMPLE 9

The Object Compound was obtained according to a similar manner to that of Example 3.

IR(Nujol): 3300, 1620, 1247, 1045 $cm^{-1}$

NMR (DMSO-$d_6$, δ): 0.89(3H, t, J=6.9 Hz), 0.96(3H, d, J=6.8 Hz), 1.11(3H, d, J=5.9 Hz), 1.2–1.55(6H, m), 1.6–2.1(5H, m), 2.1–2.6(4H, m), 2.99(1H, m), 3.19 (1H, m), 3.40(1H, m), 3.74(2H, m), 3.85–4.6(14H, m), 4.65–5.40(9H, m), 6.74 (1H, d, J=8.2 Hz), 6.83(1H, dd, J=1.7 and 8.2 Hz), 6.89(1H, s), 7.03(2H, d, J=8.8 Hz), 7.06(1H, d, J=1.7 Hz), 7.23(1H, s), 7.43(2H, m), 7.6–7.8(1H, m), 7.67(2H, d, J=8.8

84

Hz), 7.71 (2H, d, J=8.4 Hz), 7.93 (2H, d, J=8.4 Hz), 8.06(1H, d, J=8.0 Hz), 8.58(1H, d, J=6.7 Hz), 8.84(1H, s)

FAB-MS: e/z=1245($M^+$+Na)

Elemental Analysis: Calcd for $C_{54}H_{71}N_8NaO_{21}S \cdot 5H_2O$
C; 49.39 H; 6.22 N; 8.53 Found C; 49.51 H; 6.22 N; 8.53

EXAMPLE 10

The Object Compound was obtained according to a similar manner to that of Example 3.

IR(KBr): 3300, 1632, 1249, 1047 $cm^{-1}$

NMR (DMSO-$d_6$, δ): 0.85(3H, t, J=6.7 Hz), 0.94(3H, d, J=6.7 Hz), 1.03(3H, d, J=5.7 Hz), 1.1–2.6(35H, m), 2.94(1H, m), 3.17(1H, m), 3.4(1H, m), 3.72(2H, m), 3.9–4.5 (12H, m), 4.6–5.35(9H, m), 6.72(1H, d, J=8.2 Hz), 6.79(1H, s), 6.81(1H, d, J=8.2 Hz), 7.04(1H, s), 7.19(1H, s), 7.34(2H, m), 7.67(1H, m), 8.05(2H, m), 8.83 (1H, s)

FAB-MS: e/z=1203($M^+$+Na)

Elemental Analysis: Calcd for $C_{51}H_{81}N_8NaO_{20}S \cdot 4H_2O$
C; 48.87 H; 7.16 N; 8.94 Found C; 49.17 H; 7.08 N; 8.81

EXAMPLE 11

To a solution of Starting Compound (3 g) in tetrahydrofuran (30 ml) was gradually added sodium cyanoborohydride (0.461 g) at 5° C. The mixture was stirred at 40° C. for 1 hour. The reaction mixture was pulverized with diisopropyl ether (150 ml). The precipitate was collected by filtration and dried under reduced pressure. The powder was purified by column chromatography on silica gel using dichloromethane/acetic aced/methanol water(3:1:1:1) as eluent. The fractions containing the Object Compound were combined and evaporated under reduced pressure. To the residue was added water, adjusted to pH 8.5 with 1N sodium hydroxide and subjected to column chromatography on ODS(YMC-gel ODS-AM S-50) and eluted with 60% acetonitrile aq. The fractions containing the Object Compound were combined and evaporated under reduced pressure to remove acetonitrile. The residue was lyophilized to give Object Compound (0.28 g).

NMR (DMSO-$d_6$, δ): 0.88(3H, t, J=6.8 Hz), 0.97 (3H, d, J=6.7 Hz), 1.10(3H, d, J=5.9 Hz), 1.2–1.55(8H, m), 1.7–2.6(10H, m), 2.98(1H, m), 3.22(1H, m), 3.46(1H, m) 3.64–4.62(15H, m),4.7–5.5(9H, m), 6.71(1H, d, J=8.2 Hz), 6.77(1H, dd, J=1.7 and 8.2 Hz), 6.91 (1H, s), 6.98(1H, d, J=1.7 Hz), 7.2–7.35(2H, m), 7.35–7.52(2H,m), 7.6 (1H, m), 7.74(1H, m), 7.82–8.05(3H, m), 8.18(1H, d, J=8 Hz)8.43(1H, s), 8.67(1H, d, J=6.9 Hz), 8.72(1H, s)

FAB-MS: e/z=1217 ($M^+$+Na)

Elemental Analysis: Calcd: for $C_{53}H_{71}N_8NaSO)_{20} \cdot 5H_2O$
C; 49.53 H; 6.35 N; 8.72 Found: C; 49.66 H; 6.51 N; 9.10

EXAMPLE 12

The Object Compound was obtained according to a similar manner to that of Example 11.

NMR (DMSO-$d_6$, δ): 0.9–1.2(9H, m), 1.3–1.5 (4H, m), 1.7–2.4(10H, m), 2.9–3.4 (4H, m), 3.5–3.6(1H, m), 3.7–4.1(7H, m), 4.1–4.5(8H, m), 4.7–4.8(1H, m), 4.8–4.9 (2H, d, J=6.4 Hz), 5.0–5.1(1H, m), 5.1–5.3(3H, m), 5.3–5.4(1H, m), 6.7–7.1 (6H, m), 7.23(1H, s), 7.45(1H, d, J=7.8 Hz), 7.5–7.8(5H, m), 7.94(2H, d, J=8.6 Hz), 8.17(1H, d, J=7.8 Hz), 8.61(1H, d, J=6.4 Hz), 8.71(1H, s)

FAB-MS: e/z=1215($M^+$+Na)

EXAMPLE 13

To a solution of Starting Compound (5.31 g) in trifluoroacetic acid (100 ml) was gradually added sodium cyanoborohydride (0.92 g) at ambient temperature. The mixture was stirred for an hour at the same temperature. The reaction mixture was pulverized with diisopropyl ether (750 ml). The precipitate was collected by filtration and dried under reduced pressure. The powder was subjected to column chromatography on silica gel (11) and eluted with dichloromethane/acetic aced/methanol/water(3:1:1:1). The fractions containing the Object Compound were combined and evaporated under reduced pressure to give Object Compound (2.36 g).

IR(KBr): 3300, 1628, 1201 $cm^{-1}$

NMR(DMSO-$d_6$, δ): 0.86(3H, t, J=6.6 Hz), 0.95(3H, d, J=6.7 Hz), 1.08(3H, d, J=5.9 Hz), 1.2–1.5(10H, m), 1.58–2.6(10H, m), 2.96(1H, m), 3.0–3.6(2H, m), 3.65–4.53(15H, m), 4.6–5.46 (9H, m), 6.40(1H, d, J=8.1 Hz), 6.59(1H, s), 6.61(1H, d, J=8.1 Hz), 6.87(1H, s), 6.96(2H, d, J=8.9 Hz), 7.15–7.75(3H, m) 7.84(2H, d, J=8.9 Hz), 8.12(1H, m), 8.43(1H, m)

FAB-MS: e/z=1079($M^+$+Na)

EXAMPLE 14

To a solution of Starting Compound (1.469 g) in trifluoroacetic acid (14.7 ml) was gradually added sodium cyanoborohydride (0.452 g) at ambient temperature. The mixture was stirred for an hour at the same temperature. The reaction mixture was pulverized with diethyl ether (400 ml). The precipitate was collected by filtration and dried under reduced pressure. The powder was added to water (50 ml) and adjusted to pH7 with saturated $NaHCO_3$ aqueous solution, and subjected to column chromatography on ODS (YMC-gel ODS-AM S-50) and eluted with 60% aqueous methanol. The fractions containing the Object Compound were combined and evaporated under reduced pressure to remove methanol. The residue was lyophilized to give Object Compound (0.85 g).

IR(Nujol): 3250, 1600, 1060 $cm^{-1}$

NMR(DMSO-$d_6$, δ): 0.86(3H, t, J=6.7 Hz), 0.96(3H, d, J=6.6 Hz), 1.16(3H, d, J=5.7 Hz), 1.23–1.63(8H, m), 1.63–2.1 (5H, m), 2.1–2.67(5H, m), 2.95–3.67(3H, m), 3.67–4.78(16H, m), 4.78–6.11(10H, m), 6.38(1H, d, J=7.9 Hz), 6.5–6.7(2H, m), 7.1–7.7(4H, m), 7.7–8.32(5H, m), 8.32–9.1(5H, m)

FAB-MS: e/z=1115.6 ($M^+$-HCOCOOH+Na)

Elemental Analysis: Calcd for $C_{55}H_{73}N_8NaO_{20}\cdot 5H_2O$ C; 51.63 H; 6.53 N; 8.75 Found C; 51.86 H; 6.71 N; 8.86

EXAMPLE 15

The Object Compound was obtained according to a similar manner to that of Example 14.

IR(Nujol): 3250, 1600, 1060 $cm^{-1}$

NMR(DMSO-$d_6$, δ): 0.86(3H, t, J=6.6 Hz), 0.95(3H, d, J=6.7 Hz), 1.09(3H, d, J=5.9 Hz), 1.2–1.53(10H, m), 1.59–2.1(5H, m), 2.13–2.68(4H, m), 2.96(1H, m), 3.0–3.65(2H, m), 3.7–4.55 (16H, m), 4.6–5.68(10H, m), 6.40(1H, d, J=8.1 Hz), 6.59(1H, s), 6.61(1H, d, J=8.1 Hz), 6.95(2H, d, J=8.8 Hz), 7.4(1H, d, J=7 Hz), 7.51(1H, d, J=8 Hz), 7.78(brs, 1H), 7.90(2H, d, J=8.8 Hz), 8.13(1H, d, J=7 Hz), 8.35–8.6(2H, m), 8.68(1H, s), 8.73(1H, s)

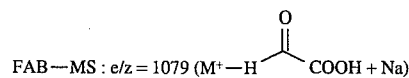

FAB—MS: e/z= 1079 ($M^+$—HCOCOOH + Na)

EXAMPLE 16

To a suspension of Starting Compound (1.0 g) and triethylsilane (0.94 g) in dichloromethane (5.0 ml) was gradually added trifluoroacetic acid (10 ml) and stirred for 30 minutes under nitrogen atmosphere. The reaction mixture was evaporated under reduced pressure. To the residue was added pH 6.86 phosphate-buffer, and adjusted to pH 8.5 with 1N sodium hydroxide and subjected to column chromatography on ODS (YMC-gel ODS-AM S-50) and eluted with 30% acetonitrile aq. The fractions containing the Object Compound were combined and evaporated under reduced pressure to remove acetonitrile. The residue was lyophilized to give Object Compound (0.61 g).

IR(KBr): 3300, 1664, 1631, 1444, 1270, 1247, 1047 $cm^{-1}$

NMR (DMSO-$d_6$, δ): 0.89(3H, t, J=7.0 Hz), 0.96 (3H, d, J=6.8 Hz), 1.09(3H, d, J=6.3 Hz), 1.3–1.5(6H, m), 1.6–2.4(10H, m), 2.9–3.3(2H, m), 3.4–3.5(1H, m), 3.7–4.1(7H, m), 4.1–5.6(8H, m), 4.7–5.3(7H, m), 5.40(2H, d, J=7.0 Hz), 6.7–7.2(7H, m), 7.23(1H, s), 7.42(1H, d, J=8.5 Hz), 7.5–7.8(6H, m), 7.94(2H, d, J=8.4 Hz), 8.10 (1H, d,J=7.0 Hz), 8.64(1H, d, J=7.0 Hz), 8.72(1H, s)

FAB-MS: e/z=1229($M^+$+Na)

Elemental Analysis: Calcd for $C_{54}H_{71}N_8NaO_{20}S\cdot 6H_2O$ C; 49.31 H; 6.40 N; 8.61 Found C; 49.38 H; 6.36 N; 8.52

EXAMPLE 17

The Object Compound was obtained according to a similar manner to that of Example 11.

NMR(DMSO-$d_6$, δ): 0.86(3H, t, J=6.8 Hz), 0.96(3H, d, J=6.7 Hz), 1.09(3H, d, J=6.0 Hz), 1.2–1.5(12H, m), 1.6–2.5(8H, m), 2.9–3.5(4H, m), 3.7–4.1(5H, m), 4.1–4.5(8H, m), 4.7–4.5(7H, m), 6.7–7.1(6H, m), 7.24(1H, s), 7.40(1H, d, J=8.4 Hz), 7.5–7.8(6H, m), 7.94(2H, d, J=8.4 Hz), 8.12(1H, d, J=8.4 Hz), 8.61(1H, d, J=7.7 Hz), 8.72(1H, s),

FAB-MS: e/z=1271.1($M^+$+Na)

Elemental Analysis: Calcd for $C_{57}H_{77}N_8NaO_{20}S\cdot 7H_2O$ C; 49.78 H; 6.67 N; 8.15 Found C; 49.94 H; 6.80 N; 8.16

EXAMPLE 18

The Object Compound was obtained according to a similar manner to that of Example 11.

IR(KBr-Pelet): 1631, 1537, 1515, 1494, 1440, 1245, 1045, 804 $cm^{-1}$

NMR(DMSO-$d_6$, δ): 0.88–1.07(15H, m), 1.10–1.18 (4H, d, J=6.3 Hz), 1.2–1.4(2H, m), 1.5–1.9(2H, m), 2.2–2.4(2H, m), 2.9–3.1(1H, m), 3.1–3.3(2H, m), 3.7–3.9(1H, m), 3.9–4.1(6H, m), 4.2–4.6(7H, m), 5.7–5.8(1H, m), 4.90(2H, d, J=6.4 Hz), 5.0–5.1(1H, m), 5.1–5.2 (4H, m), 5.3–5.4(1H, m), 6.7–6.8( 2H, m), 6.86(1H, s), 6.99(2H, s), 7.03 (2H, d, J=8.8 Hz), 7.22(1H, s), 7.4–7.5 (1H, m), 7.6–7.8(6H, m), 7.95 (3H, d, J=8.8 Hz), 8.2(1H, m), 8.6(1H, d, J=8.2 Hz), 8.76(1H, s)

FAB-MS: e/z=1229($M^+$+Na)

Elemental Analysis: Calcd for $C_{54}H_{71}N_5NaO_{20}S\cdot 6H_2O$ C; 49.31 H; 6.36 O; 8.52 Found C; 49.12 H; 6.22 O; 8.48

EXAMPLE 19

To a suspension of Starting Compound (10 g) and sodium cyanoborohydride (1.25 g) in dichloromethane (100 ml) was gradually added tetrahydrofuran (50 ml) at 5° C. The mixture was stirred at 5° C. for 1 hour. The reaction mixture was evaporated under reduced pressure. To the residue was added water, adjusted to pH 8.5 with 1N sodium hydroxide and subjected to column chromatography on ODS (YMCgel ODS-AM S-50) and eluted with 60% acetonitrile aq. The fractions containing the crude product were combined and evaporated under reduced pressure to remove acetonitrile. The residue was lyophilized to give crude powder (9.7 g). The crude powder (1.5 g) was purified by preparative HPLC utilizing a $C_{18\mu}$ Bondapak resin (Waters Associates, Inc.) which was eluted with a solvent system comprised of acetonitorile pH7 phosphate buffer (40:60) at a flow rate of 100 ml/min using a Shimazu LC-8A pump. The column was monitored by a UV detector set at 240 nm. The fractions containing the major compound at retention time of 24.1 minute were combined and evaporated under reduced pressure to remove acetonitorile. The residue was adjusted to pH 8.5 with 1N sodium hydroxide and subjected to column chromatography on ODS(YMC-gel ODS-AM S-50) and eluted with 60% acetonitorile aq. The fractions containing the Object Compound were combined and evaporated under reduced pressure to remove acetonitrile. The residue was lyophilized to give major Object Compound (0.77 g).

The minor Object Compound (98 mg) at retention time of 29.86 min. was obtained according to a similar manner to that of the major Object Compound.

Object Compound (major compound)

NMR (DMSO-$d_6$, δ): 0.88(3H, t, J 6.7 Hz), 0.96 (3H, d, J=6.7 Hz), 1.11 (3H, d, J=5.8 Hz), 1.2–1.6(8H, m), 1.62–2.13(5H, m), 2.13–2.62(4H, m), 2.97(1H, m), 3.18(1H, m), 3.40(1H, m), 3.74(2H, m), 3.83–4.63(14H, m), 4.63–5.40(9H, m), 6.73(1H, d, J=8.2 Hz), 6.81 (1H, dd, J=1.7, and 8.2 Hz), 6.89 (1H, s), 7.03(2H, d, J=8.9 Hz), 7.06(1H, d, J=1.7 Hz), 7.22(1H, s), 7.41(2H, m), 7.6–7.8(1H, m), 7.67(2H, d, J=8.9 Hz), 7.71 (2H, d, J=8.4 Hz), 7.93(2H, d, J=8.4 Hz), 8.05 (1H, d, J=8 Hz), 8.61 (1H, d, J=6.7 Hz), 8.84 (1H, s)

IR (Nujol): 3300, 1625, 1240, 1045 cm$^{-1}$

FAB-MS: e/z =1259(M$^+$+Na)

Elemental Analysis: Calcd. for $C_{55}H_{73}N_8NaO_{21}S\cdot 6H_2O$ C; 49.10 H; 6.37 N; 8.33 Found: C; 49.02 H; 6.32 N; 8.34

Object Compound (minor compound)

IR (Nujol): 3300, 1620, 1245 cm$^{-1}$ NMR (DMSO-$d_6$, δ): 0.88 (3H,t,J=6.7 Hz),0.97 (3H,d,J=6.7 Hz) 1.09 (3H,d,J=5.8 Hz),1.18–1.52 (8H,m),1.6–2.59 (10H,m),2.97 (1H,m), 3.18 (1H,m),3.40 (1H,m),3.65–4.59 (15H,m),4.65–5.45 (9H,m), 6.71 (1H,d,J=8.1 Hz),6.76 (1H,dd,J=1.7 and 8.1 Hz),6.87 (1H,s),6.97 (1H,d,J=1.7 Hz),7.03 (2H,d,J=8.8 Hz),7.21 (1H, s),7.41 (1H,d,J=7.6 Hz), 7.60 (1H,m),7.63–7.8 (1H,m),7.67 (2H,d,J=8.8 Hz),7.71 (2H,d,J=8.4 Hz), 7.94 (2H,d,J=8.4 Hz),8.10 (1H,d,J=8 Hz),8.59 (1H,d,J=8 Hz), 8.72 (1H,s)

FAB-MS: e/z=1243 (M$^+$+Na)

Elemental Analysis: Calcd: for $C_{55}H_{73}N_8NaO_{20}S\cdot 7H_2O$ C; 49.03 H; 6.51 N; 8.32 Found: C; 49.24 H; 6.25 N; 8.44

EXAMPLE 20

To a mixture of Starting Compound (1 g) and mercaptoacetic acid (290 μl) was added trifluoroacetic acid (10 ml), and the mixture was stirred at room temperature for 16 hours under nitrogen atmosphere. The mixture was evaporated under reduced pressure. The residue was poured into water (10 ml), and filtrated. The precipitate was subjected to column chromatography on silica gel using dichloromethane/acetic acid/methanol/water(3:1:1:1) as eluent. The fractions containing the Object Compound was combined and evaporated under reduced pressure. The residue was adjusted to pH8.0 with 1N sodium hydroxide and subjected to column chromatography on ODS (YMC-gel ODS-AMS50) and eluted with $CH_3CN-H_2O$ (60–40). The fractions containing the Object Compound were combined and evaporated under reduced pressure to remove acetonitrile. The residue was lyophilized to give Object Compound (515 mg).

IR (Nujol): 3300, 1662, 1627, 1203 cm$^{-1}$

FAB-MS: e/z=1205 (M$^+$)

Elemental Analysis: Calcd for $C_{55}H_{73}N_8NaO_{19}S\cdot 5H_2O$ C; 51.00 H; 6.46 N; 8.65 Found C; 51.15 H; 6.35 N; 8.56

EXAMPLE 21

The Object Compound was obtained according to a similar manner to that of Example 20.

IR (Nujol): 3300, 1672, 1658, 1629, 1530, 1438, 1270, 1214 cm$^{-1}$

FAB-MS: e/z=1220 (M$^+$+1)

Elemental Analysis: Calcd for $C_{55}H_{87}N_8NaO_{25}S\cdot 6H_2O$ C; 50.67 H; 6.61 N; 8.44 Found C; 50.67 H; 6.47 N; 8.38

EXAMPLE 22

To a solution of Starting Compound (2 g) in dimethyl formamide (20 ml) in presence of Molecular Sieves 4 Å was added glyoxylic acid (0.744 g) at ambient temperature. The mixture was stirred for 7 hours at the same temperature. The reaction mixture was pulverized with ethyl acetate. The precipitate was collected by filtration and dried under reduced pressure. The powder was added to water and adjusted to pH7.5. The solution was subjected to column chromatography on ODS (YMC-gel ODS-AM S-50) and eluted with 20% acetonitrile aq. The fractions containing the Object Compound were combined and evaporated under reduced pressure to remove acetonitrile. The residue was lyophilized to give Object Compound (1.26 g).

IR (KBr, Pellet): 3350, 1658, 1631, 1248 cm$^{-1}$

NMR (DMSO-$d_6$, δ): 0.88 (3H, t, J=6.6 Hz), 0.95 (3H, d, J=6.6 Hz) 1.18 (3H, d, J=5.5 Hz), 1.23–1.55 (8H, m,), 1.55–2.6 (9H, m), 3.09 (1H, m), 3.1–3.5 (2H, m), 3.6–5.8 (27H, m), 6.74 (1H, d, J=8.2 Hz), 6.83 (1H, d, J=8.2 Hz), 7.03 (2H, d, J=8.8 Hz), 7.05 (1H, s), 7.23–7.55 (3H, m), 7.68 (2H, d, J=8.7 Hz), 7.72 (2H, d, J=8.4 Hz), 7.96 (2H, d, J=8.4 Hz), 8.0–8.2 (2H, m), 8.45 (1H, m), 8.84 (1H, s)

FAB-MS: e/z=1259 (M$^+$+Na)

Incidentally, it is to be noted that the known compound [A] of the following formula or a salt thereof can be converted to the 30 compound [B] of the following formula or a salt thereof according to the similar manners to those of the Processes 1 and 5.

[Structure [A] or a salt thereof]

[Structure [B] or a salt thereof]

wherein

R$^a$ is acyl group,

R$^b$, R$^c$, R$^f$, and R$^g$ are each independently hydrogen or hydroxy,

R$^d$ is hydroxy, acyloxy, phosphoryloxy or sulfonyloxy,

R$^e$ is hydrogen or methyl,

R$_1^f$ is hydrogen or lower alkoxy, and

R$^h$ is lower alkyl which may have one or more suitable substituent(s),

The compound [A] was disclosed, for example, in Japanese laid-open No. 1-163179, 3-163096, 4-217694, 4-217695, 4-217696, 4-217697, 4-217698, and 4-217699.

What we claim is:

1. A polypeptide compound having improved antifungal activity of the following general formula:

[Structure [I]]

wherein

R$^1$ is hydrogen,

R$^2$ is acyl group,

R$^3$ is hydroxy or acyloxy,

R$^4$ is hydroxy or hydroxysulfonyloxy,

R$^5$ is hydrogen or lower alkyl which may have one or more suitable substituent(s), and R$^6$ is hydrogen, hydroxy or acyl (lower) alkylthio and a pharmaceutically acceptable salt thereof.

2. A compound of claim 1, wherein

R$^2$ is aroyl which may have one or more i) lower alkoxy, ii) higher alkoxy or iii) aryl which may have one or more lower alkoxy or higher alkoxy, higher alkanoyl, and R$^5$ is hydrogen or lower alkyl which may have one or more suitable substituent(s) selected from the group consisting of hydroxy, acyl, di(lower) alkyl amino and cyclic amino.

3. A compound of claim 2, wherein

R$^2$ is benzoyl or naphthoyl, each of which may have 1 to 3 suitable substituent(s) selected from the group consisting of lower alkoxy; higher alkoxy; and phenyl which may have 1 to 3 higher alkoxy;

R$^3$ is hydroxy,

R$^5$ is hydrogen, and

R$^6$ is hydrogen or hydroxy.

4. A compound of claim 3, wherein

R$^2$ is benzoyl having higher alkoxy, benzoyl having phenyl which has higher alkoxy, naphthoyl having lower alkoxy, or naphthoyl having higher alkoxy, and R$^6$ is hydrogen.

5. A compound of claim 3, wherein

R$^2$ is benzoyl having higher alkoxy, benzoyl having phenyl which has higher alkoxy, naphthoyl having lower alkoxy, or naphthoyl having higher alkoxy, and R$^6$ is hydroxy.

6. A pharmaceutical composition which comprises, as an active ingredient, a compound of claim 1 or a pharmaceutically acceptable salt thereof in admixture with a pharmaceutically acceptable carrier or excipient.

7. A method for the prophylactic and/or the therapeutic treatment of infectious diseases caused by pathogenic microorganism which comprises administering a compopund of claim 1 or a pharmaceutically acceptable salt thereof to a human being or an animal.

\* \* \* \* \*